US012774439B2

(12) United States Patent
Marchiando et al.

(10) Patent No.: US 12,774,439 B2
(45) Date of Patent: Oct. 27, 2026

(54) SYSTEMS AND METHODS FOR ENHANCED TRANSDUCTION

(71) Applicant: Cellares Corporation, South San Francisco, CA (US)

(72) Inventors: Amanda M. Marchiando, San Francisco, CA (US); Henry D. Nguyen, San Jose, CA (US); Wilson Wai Toy, San Francisco, CA (US)

(73) Assignee: Cellares Corporation, South San Francisco, CA (US)

(*) Notice: Subject to any disclaimer, the term of this patent is extended or adjusted under 35 U.S.C. 154(b) by 0 days.

(21) Appl. No.: 18/988,628

(22) Filed: Dec. 19, 2024

(65) Prior Publication Data

US 2025/0207076 A1 Jun. 26, 2025

Related U.S. Application Data

(60) Provisional application No. 63/612,987, filed on Dec. 20, 2023.

(51) Int. Cl.
*C12M 1/00* (2006.01)
*B01L 3/00* (2006.01)
(Continued)

(52) U.S. Cl.
CPC ............ *C12M 23/42* (2013.01); *C12M 23/40* (2013.01); *C12M 23/44* (2013.01); *C12M 29/14* (2013.01);
(Continued)

(58) Field of Classification Search
CPC ....... C12M 23/44; C12M 23/40; C12M 23/42
See application file for complete search history.

(56) References Cited

U.S. PATENT DOCUMENTS 3,728,227 A 4/1973 Elson et al.
4,234,023 A 11/1980 Sogi et al.
(Continued)

FOREIGN PATENT DOCUMENTS

CN 104203333 A 12/2014
CN 108660060 A 10/2018
(Continued)

OTHER PUBLICATIONS

ChargePoint (2021). Aseptic split butterfly valve 10-6 sterility assurance, located at https://www.thechargepoint.com/products/aseptic-split-butterfly-valve-10-6-sterility-assurance/, 2 total pages.
(Continued)

*Primary Examiner* — Nathan A Bowers
(74) *Attorney, Agent, or Firm* — Cooley LLP

(57) ABSTRACT

Described herein are systems and methods for automated cell transduction within a cell processing system. A system for cell processing may include a cell processing cartridge having a transduction system. The transduction system may include a fluidic manifold, one or more modules for performing a cell processing protocol, and a tube having a surface area to volume ration of between about 1,260 $mm^2/mL$ and about 5,080 $mm^2/mL$. A method for cell processing may first include flowing cells through a tube of a flow cell of a cell processing cartridge for a first time period to achieve a transduction efficiency of at least 50%. Second, the method may include expanding the cells within a bioreactor module of the cell processing cartridge for a second time period.

12 Claims, 11 Drawing Sheets

(51) Int. Cl.
*C12M 1/12* (2006.01)
*C12M 1/34* (2006.01)
*C12M 3/00* (2006.01)
*C12N 5/0783* (2010.01)
*C12N 15/86* (2006.01)

(52) U.S. Cl.
CPC ............ *C12M 37/04* (2013.01); *C12M 41/36* (2013.01); *C12N 5/0636* (2013.01); *C12N 15/86* (2013.01); *C12N 2740/15043* (2013.01)

(56) References Cited

U.S. PATENT DOCUMENTS

| | | | | |
|---|---|---|---|---|
| 4,696,902 | A | 9/1987 | Bisconte | |
| 4,839,292 | A | 6/1989 | Cremonese | |
| 4,911,833 | A | 3/1990 | Schoendorfer et al. | |
| 5,058,619 | A | 10/1991 | Zheng | |
| 5,656,491 | A | 8/1997 | Cassani et al. | |
| 6,374,684 | B1 | 4/2002 | Dority | |
| 6,649,419 | B1 | 11/2003 | Anderson | |
| 6,773,669 | B1 * | 8/2004 | Holaday | A61K 35/18 435/173.6 |
| 7,521,224 | B2 | 4/2009 | Johnson et al. | |
| 7,550,287 | B2 | 6/2009 | Hibino et al. | |
| 7,745,209 | B2 | 6/2010 | Martin et al. | |
| 7,816,128 | B2 | 10/2010 | Nakashima et al. | |
| 8,158,426 | B2 | 4/2012 | Wilson et al. | |
| 8,158,427 | B2 | 4/2012 | Wilson et al. | |
| 8,168,432 | B2 | 5/2012 | Wilson et al. | |
| 8,273,572 | B2 | 9/2012 | Martin et al. | |
| 8,415,144 | B2 | 4/2013 | Wilson et al. | |
| 8,440,458 | B2 | 5/2013 | Zijlstra et al. | |
| 8,470,589 | B2 | 6/2013 | Martin et al. | |
| 8,492,140 | B2 | 7/2013 | Smith et al. | |
| 8,546,142 | B2 | 10/2013 | Martin et al. | |
| 8,671,964 | B2 | 3/2014 | Py | |
| 8,697,443 | B2 | 4/2014 | Wilson et al. | |
| 8,727,132 | B2 | 5/2014 | Miltenyi et al. | |
| 8,809,044 | B2 | 8/2014 | Wilson | |
| 8,846,399 | B2 | 9/2014 | Martin et al. | |
| 8,956,860 | B2 | 2/2015 | Vera et al. | |
| 9,040,290 | B2 | 5/2015 | Martin et al. | |
| 9,045,721 | B2 | 6/2015 | Martin et al. | |
| 9,080,149 | B2 | 7/2015 | Bosio et al. | |
| 9,255,243 | B2 | 2/2016 | Wilson et al. | |
| 9,279,099 | B2 | 3/2016 | Okano et al. | |
| 9,290,730 | B2 | 3/2016 | Martin et al. | |
| 9,410,114 | B2 | 8/2016 | Wilson et al. | |
| 9,441,192 | B2 | 9/2016 | Wilson et al. | |
| 9,499,780 | B2 | 11/2016 | Smith et al. | |
| 9,534,195 | B2 | 1/2017 | Smith et al. | |
| 9,556,485 | B2 | 1/2017 | Lin et al. | |
| 9,567,565 | B2 | 2/2017 | Vera et al. | |
| 9,597,355 | B2 | 3/2017 | Magnant | |
| 9,625,463 | B2 | 4/2017 | Miltenyi et al. | |
| 9,701,932 | B2 | 7/2017 | Smith et al. | |
| 9,726,314 | B2 | 8/2017 | Py | |
| 9,732,317 | B2 | 8/2017 | Wilson | |
| 9,783,768 | B2 | 10/2017 | Larcher et al. | |
| 9,845,451 | B2 | 12/2017 | Martin et al. | |
| 10,047,342 | B2 | 8/2018 | Eibl et al. | |
| 10,053,663 | B2 | 8/2018 | Kabaha et al. | |
| 10,119,970 | B2 | 11/2018 | Miltenyi et al. | |
| 10,131,876 | B2 | 11/2018 | Kaiser et al. | |
| 10,253,316 | B2 | 4/2019 | Masquelier et al. | |
| 10,294,658 | B2 | 5/2019 | Scannon et al. | |
| 10,323,258 | B2 | 6/2019 | Bernate et al. | |
| 10,329,559 | B1 | 6/2019 | Masquelier et al. | |
| 10,385,307 | B2 | 8/2019 | Rowley et al. | |
| 10,421,959 | B1 | 9/2019 | Masquelier et al. | |
| 10,508,288 | B1 | 12/2019 | Bernate et al. | |
| 10,519,437 | B1 | 12/2019 | Masquelier et al. | |
| 10,533,156 | B2 | 1/2020 | Vera et al. | |
| 10,584,333 | B1 | 3/2020 | Masquelier et al. | |
| 10,584,334 | B1 | 3/2020 | Masquelier et al. | |
| 10,584,354 | B2 | 3/2020 | Wilson | |
| 10,588,994 | B2 | 3/2020 | Kawamura et al. | |
| 10,620,212 | B2 | 4/2020 | Miltenyi et al. | |
| 10,689,669 | B1 | 6/2020 | Feldman et al. | |
| 10,705,090 | B2 | 7/2020 | Miltenyi et al. | |
| 10,705,091 | B2 | 7/2020 | Miltenyi et al. | |
| 10,723,986 | B2 | 7/2020 | Smith et al. | |
| 10,724,043 | B2 | 7/2020 | Sixto et al. | |
| 10,844,338 | B1 | 11/2020 | Smith et al. | |
| 11,161,111 | B2 | 11/2021 | Kabaha et al. | |
| 11,198,845 | B2 | 12/2021 | Parietti et al. | |
| 11,371,018 | B2 | 6/2022 | Shi et al. | |
| 11,376,587 | B2 | 7/2022 | Thakkar et al. | |
| 11,447,745 | B2 | 9/2022 | Shi et al. | |
| 11,613,725 | B2 | 3/2023 | Wilson et al. | |
| 11,701,654 | B2 | 7/2023 | Azersky et al. | |
| 11,786,896 | B2 | 10/2023 | Thakkar et al. | |
| 11,826,756 | B2 | 11/2023 | Azersky et al. | |
| 11,872,557 | B2 | 1/2024 | Biz et al. | |
| 12,157,119 | B2 | 12/2024 | Gerlinghaus et al. | |
| 12,180,453 | B2 | 12/2024 | Chang et al. | |
| 12,305,156 | B2 | 5/2025 | Burkeen et al. | |
| 12,337,321 | B2 | 6/2025 | Malleo et al. | |
| 12,350,664 | B2 | 7/2025 | Pesch et al. | |
| 12,350,667 | B2 | 7/2025 | Azersky et al. | |
| 12,350,668 | B2 | 7/2025 | Azersky et al. | |
| 12,399,193 | B2 | 8/2025 | Tian et al. | |
| 12,403,468 | B2 | 9/2025 | Azersky et al. | |
| 12,491,512 | B2 | 12/2025 | Biz et al. | |
| 12,492,368 | B2 | 12/2025 | Carmichael et al. | |
| 12,497,587 | B2 | 12/2025 | Grout et al. | |
| D1,109,621 | S | 1/2026 | Cesarek et al. | |
| 12,551,887 | B2 | 2/2026 | Biz et al. | |
| 12,559,710 | B2 | 2/2026 | Azersky et al. | |
| 12,570,948 | B2 | 3/2026 | Thakkar et al. | |
| 2002/0146817 | A1 | 10/2002 | Cannon et al. | |
| 2003/0030272 | A1 | 2/2003 | Johnson et al. | |
| 2004/0121454 | A1 * | 6/2004 | Jury | B01F 25/433 435/288.5 |
| 2005/0070018 | A1 | 3/2005 | Johnson et al. | |
| 2005/0186671 | A1 | 8/2005 | Cannon et al. | |
| 2005/0260743 | A1 | 11/2005 | Drake et al. | |
| 2006/0194193 | A1 | 8/2006 | Tsuruta et al. | |
| 2006/0257999 | A1 | 11/2006 | Chang et al. | |
| 2007/0185472 | A1 | 8/2007 | Baumfalk et al. | |
| 2008/0057568 | A1 | 3/2008 | Kan et al. | |
| 2008/0176318 | A1 | 7/2008 | Wilson et al. | |
| 2009/0042281 | A1 | 2/2009 | Chang et al. | |
| 2009/0053799 | A1 | 2/2009 | Chang-Yen et al. | |
| 2009/0247417 | A1 | 10/2009 | Haas et al. | |
| 2010/0130732 | A1 | 5/2010 | Chung et al. | |
| 2010/0151571 | A1 | 6/2010 | Vukasinovic et al. | |
| 2011/0003380 | A1 | 1/2011 | Miltenyi et al. | |
| 2011/0229927 | A1 | 9/2011 | Larsen et al. | |
| 2012/0138156 | A1 | 6/2012 | Hofman et al. | |
| 2013/0115617 | A1 | 5/2013 | Wilson | |
| 2014/0309795 | A1 | 10/2014 | Norton et al. | |
| 2015/0307829 | A1 | 10/2015 | Dedry et al. | |
| 2015/0336096 | A1 | 11/2015 | Smith et al. | |
| 2016/0208216 | A1 | 7/2016 | Vera et al. | |
| 2016/0244714 | A1 | 8/2016 | Spuhler et al. | |
| 2016/0303563 | A1 | 10/2016 | Granier et al. | |
| 2016/0320381 | A1 | 11/2016 | Holmes et al. | |
| 2016/0320422 | A1 | 11/2016 | Fritchie et al. | |
| 2017/0058257 | A1 | 3/2017 | Levner et al. | |
| 2017/0058527 | A1 | 3/2017 | Williams et al. | |
| 2017/0307502 | A1 | 10/2017 | Mason et al. | |
| 2017/0313977 | A1 | 11/2017 | Wilson | |
| 2017/0321226 | A1 | 11/2017 | Gill et al. | |
| 2017/0348525 | A1 | 12/2017 | Sano et al. | |
| 2017/0362554 | A1 | 12/2017 | Martin et al. | |
| 2018/0031592 | A1 | 2/2018 | Dority | |
| 2018/0051243 | A1 * | 2/2018 | Hogan | C12M 41/46 |
| 2018/0078935 | A1 | 3/2018 | Hung et al. | |
| 2018/0196918 | A1 | 7/2018 | Sadowski et al. | |
| 2019/0002874 | A1 | 1/2019 | Belgrader et al. | |
| 2019/0144826 | A1 | 5/2019 | Leen et al. | |
| 2019/0212233 | A1 | 7/2019 | Jovanovich et al. | |
| 2019/0264176 | A1 | 8/2019 | Leen et al. | |

(56) References Cited

U.S. PATENT DOCUMENTS

| | | | |
|---|---|---|---|
| 2019/0275519 | A1 | 9/2019 | Castillo et al. |
| 2019/0292510 | A1 | 9/2019 | Tandon et al. |
| 2019/0293673 | A1 | 9/2019 | Wescott et al. |
| 2019/0316120 | A1 | 10/2019 | Masquelier et al. |
| 2019/0330579 | A1 | 10/2019 | Guenat et al. |
| 2019/0345444 | A1 | 11/2019 | Rosenberg et al. |
| 2020/0009557 | A1 | 1/2020 | Frigard et al. |
| 2020/0025782 | A1 | 1/2020 | Ahlfors |
| 2020/0048599 | A1 | 2/2020 | Firouzi et al. |
| 2020/0095550 | A1 | 3/2020 | Vera et al. |
| 2020/0159198 | A1 | 5/2020 | Kapre et al. |
| 2020/0224147 | A1 | 7/2020 | Rogers et al. |
| 2020/0283713 | A1 | 9/2020 | Ball et al. |
| 2020/0292552 | A1 | 9/2020 | Miltenyi et al. |
| 2020/0353004 | A1 | 11/2020 | Nowak et al. |
| 2020/0368411 | A1 | 11/2020 | Camisani et al. |
| 2020/0399578 | A1 | 12/2020 | Corso et al. |
| 2020/0406221 | A1 | 12/2020 | Dabrowski et al. |
| 2021/0001339 | A1 | 1/2021 | Liu et al. |
| 2021/0032583 | A1 | 2/2021 | Smith et al. |
| 2021/0035655 | A1 | 2/2021 | Tanouchi et al. |
| 2021/0047668 | A1 | 2/2021 | Dabrowski et al. |
| 2021/0079344 | A1 | 3/2021 | Bosio et al. |
| 2021/0147807 | A1 | 5/2021 | Lickert et al. |
| 2021/0253997 | A1 | 8/2021 | Wilson |
| 2021/0269755 | A1 | 9/2021 | Smith et al. |
| 2021/0283565 | A1 | 9/2021 | Gerlinghaus et al. |
| 2021/0283606 | A1 | 9/2021 | Thakkar et al. |
| 2021/0284948 | A1 | 9/2021 | Hauwaerts et al. |
| 2021/0301239 | A1 | 9/2021 | Natsume et al. |
| 2021/0324318 | A1 | 10/2021 | Parietti et al. |
| 2021/0354104 | A1 | 11/2021 | Pesch et al. |
| 2022/0047862 | A1 | 2/2022 | Chang et al. |
| 2022/0127558 | A1 | 4/2022 | Sowwan et al. |
| 2022/0143610 | A1 | 5/2022 | Biz et al. |
| 2022/0150650 | A1 | 5/2022 | Rucker |
| 2022/0282199 | A1 | 9/2022 | Vann |
| 2022/0325219 | A1 | 10/2022 | Parietti et al. |
| 2022/0325240 | A1* | 10/2022 | McFarland ............ A61K 40/11 |
| 2022/0347683 | A1 | 11/2022 | Thakkar et al. |
| 2023/0051840 | A1* | 2/2023 | Kelso ..................... C12M 45/07 |
| 2023/0149922 | A1 | 5/2023 | Thakkar et al. |
| 2023/0321650 | A1 | 10/2023 | Azersky et al. |
| 2023/0415154 | A1 | 12/2023 | Pesch et al. |
| 2023/0415155 | A1 | 12/2023 | Biz et al. |
| 2024/0165613 | A1 | 5/2024 | Azersky et al. |
| 2024/0254426 | A1 | 8/2024 | Elpel et al. |
| 2024/0255537 | A1 | 8/2024 | Malleo et al. |
| 2024/0279585 | A1* | 8/2024 | Griffin ................... C12M 33/14 |
| 2024/0279588 | A1 | 8/2024 | Malleo et al. |
| 2024/0318116 | A1 | 9/2024 | Chang et al. |
| 2024/0326043 | A1 | 10/2024 | Gerlinghaus et al. |
| 2024/0369586 | A1 | 11/2024 | Tian et al. |
| 2024/0377420 | A1 | 11/2024 | Cesarek |
| 2024/0390897 | A1 | 11/2024 | Azersky et al. |
| 2024/0390898 | A1 | 11/2024 | Azersky et al. |
| 2024/0399365 | A1 | 12/2024 | Biz et al. |
| 2024/0402206 | A1 | 12/2024 | Boppart et al. |
| 2025/0002837 | A1 | 1/2025 | Thakkar et al. |
| 2025/0059492 | A1 | 2/2025 | Beban et al. |
| 2025/0065331 | A1 | 2/2025 | Malleo et al. |
| 2025/0066708 | A1 | 2/2025 | Burkeen et al. |
| 2025/0066709 | A1 | 2/2025 | Grout et al. |
| 2025/0129321 | A1 | 4/2025 | Malleo et al. |
| 2025/0236832 | A1 | 7/2025 | Chang et al. |
| 2025/0283026 | A1 | 9/2025 | Carmichael et al. |
| 2025/0304904 | A1 | 10/2025 | Azersky et al. |
| 2025/0360504 | A1 | 11/2025 | Azersky et al. |
| 2025/0367660 | A1 | 12/2025 | Biz et al. |
| 2025/0368943 | A1 | 12/2025 | Burkeen et al. |
| 2025/0375767 | A1 | 12/2025 | Malleo et al. |
| 2026/0029422 | A1 | 1/2026 | Malleo et al. |
| 2026/0056220 | A1 | 2/2026 | Tian et al. |

FOREIGN PATENT DOCUMENTS

| | | | | |
|---|---|---|---|---|
| EP | 0246912 | A2 | 11/1987 | |
| EP | 0991389 | A1 | 4/2000 | |
| EP | 0824380 | B1 | 1/2002 | |
| EP | 3134512 | B1 | 1/2019 | |
| EP | 2809449 | B1 | 10/2019 | |
| EP | 3359294 | B1 | 5/2020 | |
| EP | 3928867 | A1 | 12/2021 | |
| GB | 2268187 | A | 1/1994 | |
| JP | 2007325586 | A | 12/2007 | |
| KR | 20130018286 | A | 2/2013 | |
| KR | 20220131302 | A | 9/2022 | |
| WO | WO-2006102416 | A2 | 9/2006 | |
| WO | WO-2006112870 | A1 | 10/2006 | |
| WO | WO-2006118282 | A1 | 11/2006 | |
| WO | WO-2007139742 | A1 | 12/2007 | |
| WO | WO-2009072003 | A2 | 6/2009 | |
| WO | WO-2017041051 | A1 | 3/2017 | |
| WO | WO-2017123663 | A1 | 7/2017 | |
| WO | WO-2017190790 | A1 * | 11/2017 | ............ C12M 23/28 |
| WO | WO-2018015561 | A1 | 1/2018 | |
| WO | WO-2018102471 | A1 | 6/2018 | |
| WO | WO-2019232504 | A2 | 12/2019 | |
| WO | WO-2020009700 | A1 | 1/2020 | |
| WO | WO-2020014264 | A1 | 1/2020 | |
| WO | WO-2021168368 | A1 | 8/2021 | |
| WO | WO-2021183687 | A2 | 9/2021 | |
| WO | WO-2021212124 | A1 | 10/2021 | |
| WO | WO-2022137061 | A1 * | 6/2022 | ............. C12N 15/86 |
| WO | WO-2023064187 | A1 * | 4/2023 | ............. C12N 15/86 |
| WO | WO-2024112702 | A1 | 5/2024 | |
| WO | WO-2024197093 | A2 | 9/2024 | |
| WO | WO-2025038974 | A1 | 2/2025 | |
| WO | WO-2025041046 | A1 | 2/2025 | |
| WO | WO-2025041047 | A1 | 2/2025 | |
| WO | WO-2025041064 | A2 | 2/2025 | |

OTHER PUBLICATIONS

CPC (2014). "6 traits of non-spill: How quick disconnect couplings evolved for low-pressure fluid handling," White Paper 8004, 4 total pages.

CPC (2014). "How single-use connections advance aseptic processing: Increased process flexibility and reliability, reduced costs," White Paper 7004, 6 total pages.

CPC (2018). Comparison Guide: Tube Welders and Aseptic Connectors, Technical Guide 7009, 3 total pages.

EMD Millipore (2015). "Lynx® S2S Connector—Low temperature compatibility (-80"C)," 4 total pages.

Final Office Action for U.S. Appl. No. 17/331,554 mailed Aug. 29, 2024, 18 pages.

Final Office Action for U.S. Appl. No. 18/652,602 mailed Nov. 1, 2024, 29 pages.

Final Office Action mailed on Apr. 28, 2022, for U.S. Appl. No. 17/198,134, filed Mar. 10, 2021, 11 pages.

Final Office Action mailed on Apr. 28, 2022, for U.S. Appl. No. 17/331,554, filed May 26, 2021, 16 pages.

Final Office Action mailed on Jul. 31, 2023, for U.S. Appl. No. 17/331,554, filed May 26, 2021, 19 pages.

Final Office Action mailed on Mar. 31, 2023, for U.S. Appl. No. 17/579,478, filed Jan. 19, 2022, 8 pages.

Garcia et al., "Microfluidic Screening of Electric Fields for Electroporation" Sci Rep. Feb. 19, 2016; 6:21238. pp. 1-11.

Genetic Engineering & Biotechnology News (2006). "Thermal welding for sterile connections," located at https://www.genengnews.com/magazine/47/thermal-welding-for-sterile-connections/, 5 total pages.

International Search Report and Written Opinion for International Application No. PCT/US2023/080593 dated Mar. 21, 2024, 12 pages.

International Search Report and Written Opinion for PCT Application No. PCT/IB2024/058105 mailed Dec. 16, 2024, 12 pages.

International Search Report and Written Opinion for PCT Application No. PCT/US2024/042795 mailed Dec. 16, 2024, 11 pages.

(56) References Cited

OTHER PUBLICATIONS

International Search Report mailed on Oct. 13, 2021, for PCT Application No. PCT/US2021/021773, filed on Mar. 10, 2021, 13 pages.
Invitation to Pay Additional fees for International Application No. PCT/IB2024/058148, mailed Jan. 2, 2025, 13 pages.
Jain, S. et al. (2011). "The complete automation of cell culture: improvements for high-throughput and high-content screening," J. Biomol. Screen 16:932-939.
Kato, R. et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.
Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). INTACT™ Connectors, located at https://www.medinstill.com/intactconnectors.php, 1 total page.
Millipore® (2020). "Technical Brief- Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors,MM_NF-C188801, 2 total pages.
Non-Final Office Action for U.S. Appl. No. 18/244,051 mailed Oct. 9, 2024, 10 pages.
Non-Final Office Action for U.S. Appl. No. 18/652,602 mailed Jul. 17, 2024, 30 pages.
Non-Final Office Action for U.S. Appl. No. 18/792,358 mailed on Nov. 6, 2024, 5 pages.
Non-Final Office Action for U.S. Appl. No. 18/799,963 mailed Sep. 30, 2024, 9 pages.
Non-Final Office Action for U.S. Appl. No. 18/810,386 mailed Nov. 18, 2024, 8 pages.
Non-Final Office Action mailed on Apr. 24, 2024, for U.S. Appl. No. 17/331,554, filed May 26, 2021, 17 pages.
Non-Final Office Action mailed on Dec. 22, 2022, for U.S. Appl. No. 17/579,478, filed Jan. 19, 2022, 8 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed Mar. 10, 2021, 5 pages.
Non-Final Office Action mailed on Jun. 26, 2023, for U.S. Appl. No. 17/198,134, filed Mar. 10, 2021, 15 pages.
Non-Final Office Action mailed on Mar. 16, 2023, for U.S. Appl. No. 17/331,554, filed May 26, 2021, 16 pages.
Non-Final Office Action mailed on May 14, 2024, for U.S. Appl. No. 18/611,632, filed Mar. 20, 2024, 13 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198,134, filed Mar. 10, 2021, 7 pages.
Non-Final Office Action mailed on Sep. 13, 2023, for U.S. Appl. No. 18/141,329, filed Apr. 28, 2023, 7 pages.
Notice of Allowance (Corrected) mailed on Sep. 5, 2024, for U.S. Appl. No. 18/611,632, filed Mar. 20, 2024, 6 pages.
Notice of Allowance for U.S. Appl. No. 18/611,632 mailed Aug. 26, 2024, 9 pages.
Notice of Allowance for U.S. Appl. No. 18/810,388 mailed on Oct. 9, 2024, 9 pages.
Notice of Allowance for U.S. Appl. No. 18/811,490 mailed on Dec. 12, 2024, 8 pages.
Notice of Allowance mailed on Apr. 11, 2024, for U.S. Appl. No. 17/198,134, filed Mar. 10, 2021, 9 pages.
Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Mar. 22, 2023, for U.S. Appl. No. 17/992,784, filed Nov. 22, 2022, 8 pages.
Notice of Allowance mailed on Oct. 4, 2023, for U.S. Appl. No. 18/141,329, filed Apr. 28, 2023, 8 pages.
Pharma Japan, "Astellas Set to Cut Development Time with Cell Culture Robot, Eyes 4 Billion Yen Profit per Product" Aug. 9, 2023, 3 pages.
Qu, B. et al., "Droplet Electroporation in Microfluidics for Efficient Cell Transformation with or without Cell Wall Removal," Lab Chip (2012) 12:4483-4488.
Saint Gobain (2017). "Pure-Fit® SC—Secure aseptic connections," Brochure, 5 total pages.
Sartorius Stedim Biotech (2011). "Opta® SFT," 4 total pages.
Schwartz C., "Optimizing Cell Separation with Beckman Coulter's Centrifugal Elutriation System," Beckmann Coulter Life Sciences (2014) 6 total pages.
SeriesLock™ (2021). Features and Specifications, located at https://serieslock.com/, 5 total pages.
Shi, Y. et al. (1992). "Performance of Mammalian Cell Culture Bioreactor with a New Impeller Design," Biotechnology and Bioengineering 40:260-270.
STERIS (2018). "A compilation of material compatibilities with vaporized hydrogen peroxide," 2 total pages.
STERIS (2018). "Sterility assurance levels (SALS): Irradiation," 3 total pages.
STERIS (2020). "Overview of sterilization technology comparison," 1 total page.
Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.
U.S. Appl. No. 18/807,699, filed Aug. 16, 2024, by Beban et al.
U.S. Appl. No. 29/898,923, filed Aug. 2, 2023, by Gerlinghaus et al.
Written Opinion of the International Searching Authority mailed on Oct. 13, 2021, for PCT Application No. PCT/US2021/021773, filed on Mar. 10, 2021, 20 pages.
Final Office Action for U.S. Appl. No. 18/244,051 mailed Apr. 4, 2025, 11 pages.
Final Office Action for U.S. Appl. No. 18/799,963 mailed Jan. 30, 2025, 10 pages.
Final Office Action for U.S. Appl. No. 18/810,386 mailed on Mar. 28, 2025, 8 pages.
International Search Report and Written Opinion for International Application No. PCT/IB2024/058106 mailed Jan. 21, 2025, 13 pages.
International Search Report and Written Opinion for International Application No. PCT/IB2024/058148 mailed Mar. 3, 2025, 21 pages.
International Search Report and Written Opinion for PCT Application No. PCT/US2024/020809 mailed Mar. 24, 2025, 19 pages.
Invitation to Pay Additional fees for International Application No. PCT/US2024/020809, mailed Jan. 27, 2025, 17 pages.
Non-Final Office Action for U.S. Appl. No. 18/807,699 mailed Apr. 29, 2025, 19 pages.
Notice of Allowance for U.S. Appl. No. 17/331,554 mailed Apr. 10, 2025, 6 pages.
Notice of Allowance for U.S. Appl. No. 17/331,554 mailed Mar. 5, 2025, 8 pages.
Notice of Allowance for U.S. Appl. No. 18/487,884 mailed Feb. 26, 2025, 8 pages.
Notice of Allowance for U.S. Appl. No. 18/487,884 mailed on Apr. 3, 2025, 8 pages.

(56) References Cited

OTHER PUBLICATIONS

Notice of Allowance for U.S. Appl. No. 18/652,602 mailed May 2, 2025, 14 pages.
Notice of Allowance for U.S. Appl. No. 18/792,358 mailed on Mar. 3, 2025, 8 pages.
Notice of Allowance for U.S. Appl. No. 18/792,360 mailed Mar. 4, 2025, 9 pages.
Notice of Allowance for U.S. Appl. No. 18/792,360 mailed on Jan. 29, 2025, 9 pages.
Notice of Allowance for U.S. Appl. No. 18/810,388 mailed Apr. 30, 2025, 5 pages.
Notice of Allowance for U.S. Appl. No. 18/810,388 mailed Jan. 21, 2025, 8 pages.
Notice of Allowance for U.S. Appl. No. 18/811,490 mailed Feb. 26, 2025, 8 pages.
U.S. Appl. No. 18/244,051, Notice of Allowance mailed Oct. 15, 2025; Inventor Biz, Tony et al.; 5 pages.
U.S. Appl. No. 18/799,963, Notice of Allowance mailed Jul. 1, 2025; Inventor Biz, Tony et al.; 7 pages.
U.S. Appl. No. 18/807,699, Final Office Action mailed Aug. 20, 2025; Inventor Beban, Marc et al.; 22 pages.
U.S. Appl. No. 18/810,386, Notice of Allowance mailed Aug. 18, 2025; Inventor Grout, Wayne E et al.; 10 pages.
U.S. Appl. No. 18/244,047, Non-Final Office Action mailed May 6, 2026; Inventor Pesch; Brian Alexander et al.; 7 pages.
U.S. Appl. No. 19/295,488, Non-Final Office Action mailed Dec. 18, 2025; Inventor Biz, Tony et al.; 9 pages.
U.S. Appl. No. 19/295,488, Notice of Allowance mailed Apr. 21, 2026; Inventor Biz, Tony et al.; 7 pages.
U.S. Appl. No. 19/392,013, filed Nov. 17, 2025; Inventor Grout, Wayne E et al.
U.S. Appl. No. 19/534,547, filed Feb. 9, 2026; Inventor Thakkar, Bharat S et al.

* cited by examiner

SYSTEMS AND METHODS FOR ENHANCED TRANSDUCTION

CROSS REFERENCE TO RELATED APPLICATIONS

This application claims priority to U.S. Provisional Patent Application No. 63/612,987 filed Dec. 20, 2023, the content of which is incorporated herein by reference in its entirety for all purposes.

TECHNICAL FIELD

The present disclosure relates to systems and methods for cell transduction for biomedical applications using automated systems.

BACKGROUND

Cell processing may generally involve collecting cells from an individual, processing the cells, and utilizing the processed cells to achieve a clinical response in the same or a different individual. Cell processing may be a complex workflow that involves multiple steps, where each step typically requires a separate cell processing device and/or system to accomplish the step. Moreover, traditional solutions may rely on cumbersome manual operations performed in expensive biosafety cabinets and/or cleanrooms. Such facilities may generally require skilled laboratory technicians, adequate sterile enclosures (e.g., cleanroom facilities), and associated protocols for regulated (GMP) manufacturing, and therefore may be expensive to design and use. Further, known cell processing solutions may also employ numerous manual reagent preparation and instrument manipulation steps, even of which may each require several days or weeks. Thus, conventional solutions may require a large investment of time to complete a cell therapy manufacturing procedure. While some conventional platforms may be described as "automated" cell processing (e.g., in a closed system), these platforms may often rely on pre-configured instrumentation and tubing sets that limit operational flexibility and do not reliably prevent process failure due to human error. Indeed, most efforts to automate cell product manufacturing have focused on automating discrete steps of a cell therapy manufacturing workflow instead of the end-to-end workflow, and thus may lack end-to-end process flexibility, process robustness, and process scalability.

Furthermore, automating a cell culture protocol of a cell processing workflow may be particularly challenging due to multiple sensitive operations including cell activation, transduction and expansion. Cell transduction, for example, refers to the process by which genetic material is introduced into a cell to alter its properties or behavior. In particular, during transduction, specific genes may be inserted into activated cells of a cell population, deleted from the cells, or otherwise modified within the cells to enhance their therapeutic potential. Thus, integration of cell transduction into a cell product manufacturing system may be vital to enable precise control over cell characteristics (including their behavior, lifespan, and interactions with a patient). Moreover, considering the limitations of conventional cell therapy systems, automating a cell transduction step within an end-to-end automated cell therapy manufacturing platform may be critical for translating cell therapies to the broader patient population. Accordingly, systems and methods for enhanced cell transduction may be desirable.

SUMMARY

Described herein are systems, devices, and methods useful for cell processing. In some variations, the methods described herein may be performed by automatically by a cell processing system. In general, the methods for cell processing include flowing cells through at least one tube of a flow cell of a cell processing cartridge for a first time period to achieve a transduction efficiency of at least 50%, and expanding the cells within a bioreactor module of the cell processing cartridge for a second time period.

In some variations, following the cells through the at least one tube includes transferring the cells from a mixing chamber of the bioreactor module to the flow cell via a fluidic manifold of the cell processing cartridge, and transferring the cells from the flow cell to the mixing chamber via the fluidic manifold of the cell processing cartridge. In some variations, cells flow through the at least one tube via a fluidic manifold of the cell processing cartridge.

The transduction efficiency may be measured or it may be estimated. In some variations the transduction efficiency is equal to or greater than 60%. In some variations, the transduction efficiency is equal to or greater than 70%.

The first time period may be any suitable time period, for example, the first time period may be between about 60 minutes and about 90 minutes. Similarly, the second time period may be any suitable time period. For example, the second time period may be between about 5 days and about 7 days.

A constant flow rate of the cells through the at least one tube may be maintained over the first time period, or it may be variable. In some variations the flow rate is constant. In some variations, the flow rate is between about 5 mL/min and about 100 mL/min.

The cells used herein may be suspended in a cell solution comprising a density of between about $5\times10^5$ cells/mL and about $2\times10^6$ cells/mL, and may be any suitable cells, e.g., T-cells. The cells may be isolated from blood, e.g., via apheresis. When the cells are suspended in a cell solution, the method may further include, prior to transducing the cells, introducing one or more transduction reagents (e.g., a lentiviral vector, a virus, etc.) into the cell solution. In some variations, the tube for use with the methods described herein has a surface area to volume ratio of between about 1,260 $mm^2$/mL and about 5,080 $mm^2$/m and a diameter of between about 1.57 mm and about 3.18 mm.

Systems for cell processing are also described herein. In general, the systems include a cell processing cartridge, where the cartridge includes a transduction system. The transduction system includes a fluidic manifold, one or more modules for cell processing, and at least one tube having a surface area to volume ratio of between about 1,260 $mm^2$/mL and about 5,080 $mm^2$/mL. Any suitable number of modules may be used with the systems described herein. For example, in some variations, the one or more modules include a bioreactor module and a flow cell. The at least one tube may be coupled to the flow cell, and the bioreactor module may include a mixing chamber container configured to receive a volume of cell solution. In some variations, the at least one tube includes a diameter of between about 1.57 mm and about 3.18 mm.

The system may further include a pump configured to maintain a constant flow rate of cells through the at least one tube. In some variations, the flow rate is between about 5 mL/min and about 100 mL/min. The system may further include a docking station configured to receive the cell processing cartridge, and/or a reagent vault configured to store one or more reagents (e.g., transduction reagents) for cell processing. The system may further include a sterile liquid transfer device configured to exchange the one or more reagents between the reagent vault and the cell processing cartridge. In some variations, the sterile liquid transfer device is fluidically coupled to the fluidic manifold via a sterile liquid transfer port.

Additional embodiments, features, and advantages of the invention will be apparent from the following detailed description and through practice of the invention.

DETAILED DESCRIPTION

Figure 1A:
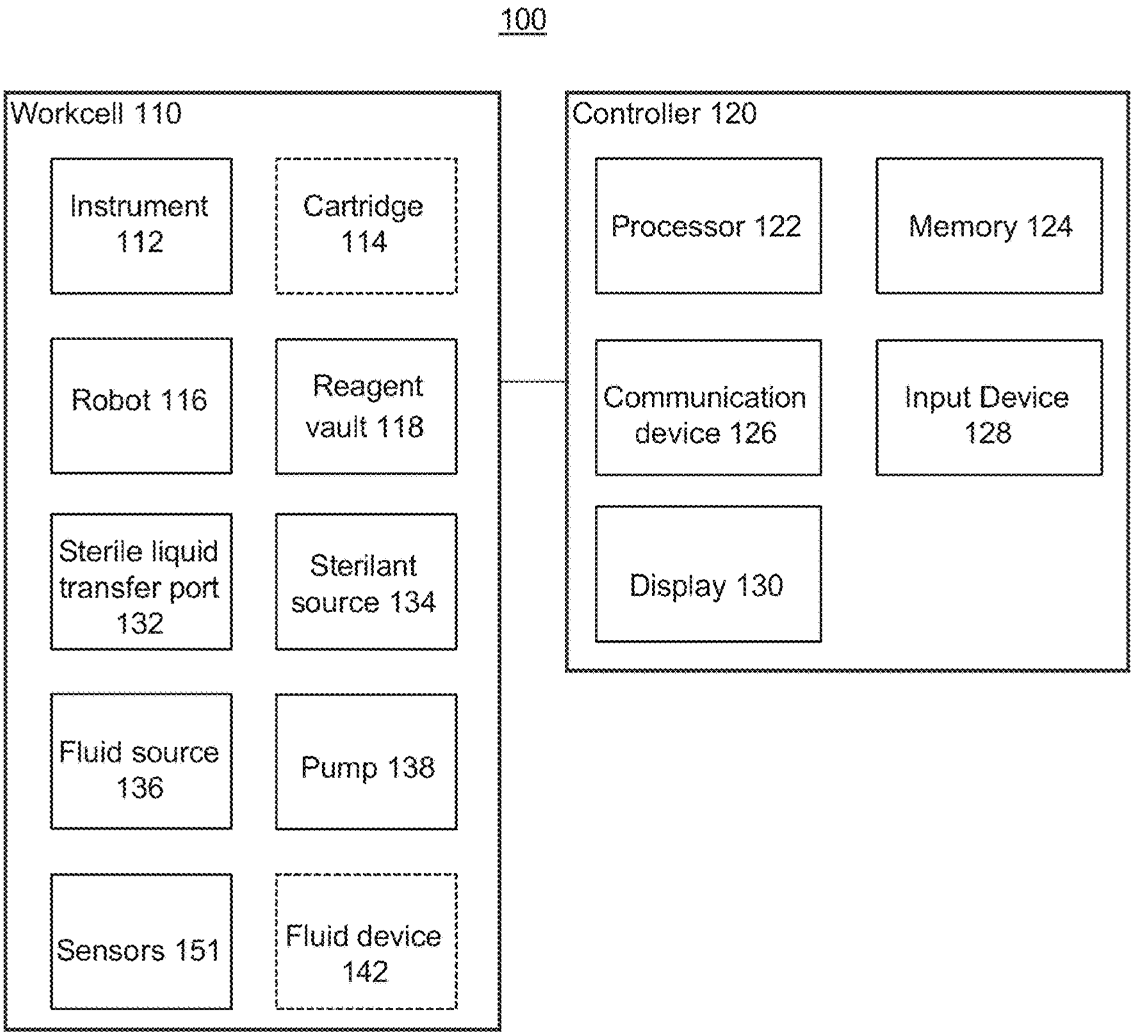
FIG. 1A is a block diagram of an illustrative variation of a cell processing system.

Disclosed herein are devices, systems, and methods for cell transduction, for example, within an automated cell processing system. Generally, the cell processing systems described herein may include a transduction system including a group of components of a cartridge of the cell processing system. For example, the transduction system may include one or more of a fluidic manifold, a tube, a pump module, a bioreactor module, and a flow cell, as described in detail herein.

To perform a transduction step of a cell processing workflow, a transduction reagent (e.g., a lentiviral vector and/or a virus) may be introduced to a cell solution. The transduction reagent may be configured to target a specific cell type. Accordingly, the quantity (e.g., volume) of the transduction reagent may correspond to a cell concentration value (e.g., number of cells per unit volume) within the cell solution. For example, a relatively large quantity of the transduction reagent may be introduced to a cell solution with a correspondingly high cell concentration, while a relatively small quantity of the transduction reagent may be introduced to a cell solution with a correspondingly low cell concentration. In this way, the quantity of transduction reagents may be approximately proportional to the concentration of target cells in the cell solution. The transduction reagent may be used to introduce, for example, a chimeric antigen receptor (CAR) to cells within the cell solution. In another example, a lentiviral vector comprising Lenti-CD19 CAR (scFv-41BB-CD3ζ, CTL019) may be configured to target CD19+ cells.

Next, after a period of time (e.g., from a few to several days, such as about 3 to about 7 days), the viral transduction efficiency (i.e., the percent of cells that express the genes of the transduction reagent) may be determined (e.g., measured or estimated) to inform whether the cells may proceed to be expanded. In some variations, the cell solution may be agitated throughout some or all of the period of time of transduction in order to increase the transduction efficiency. A conventional method for agitating the cell solution may include, for example, centrifugation.

Advantageously, to perform a transduction step of a cell processing procedure within the cell processing systems described herein, a transduction reagent may be introduced into a cell solution within the bioreactor module (e.g., within a bioreactor or a mixing chamber of the bioreactor module), and the resulting solution may be transferred back and forth between the bioreactor module and the flow cell via the tube and the fluidic manifold. As described herein, compared to conventional approaches to transduction (e.g., centrifugation, static transduction), the fluid exchange of the cell solution through the tube and between the bioreactor module and the flow cell may advantageously increase the transduction efficiency of the transduction reagent.

The transduction system described herein may be automated and may be easily integrated into the cell processing systems described herein. While conventional approaches to automated cell transduction may employ centrifugation, systems and devices configured for such processes may be difficult to integrate into an end-to-end cell processing system. Thus, traditional cell processing systems may often include manual or discretely automated transduction. In contrast, an automated end-to-end cell processing system may reduce the risk of cell product contamination and/or may reduce labor costs associated with cell therapy manufacturing due to a reduction in operator handling required as compared to a discrete approach. Indeed, integrated, automated cell product manufacturing platforms may provide numerous benefits compared to conventional approaches to cell therapy manufacturing, such as labor time and cost savings, improved product consistency, decreased room classification, decreased cleanroom footprint, decreased training complexities, and improved scale-up and tracking logistics.

Cell Processing System

The cell processing systems described herein may be configured to perform one or more cell processing steps in a workcell. The workcell may comprise a closed, automated environment, which may be configured to maintain a sterile environment. The workcell may receive a cartridge and perform one or more cell processing steps on cells in a cell solution (e.g., cell suspension) contained within the cartridge. For example, the cell processing system may include a workcell having a plurality of instruments that may each be configured to independently perform one or more cell processing steps to the cells and/or cell solution, and a robot capable of moving the cartridge within the workcell (e.g., between one or more bays). The robot and/or instruments may be configured to automatically operate such that operator assistance may not be required at any point during the workflow. For example, the robot may receive the cartridge and move the cartridge between locations (e.g., instruments, bays, storage vaults, feedthroughs) within the workcell according to a pre-programmed workflow, where each location may be associated with one or more cell processing steps. After performing one or more cell processing steps of the pre-programmed workflow, the workcell may be configured to transfer the cartridge out of the workcell (e.g., via the robot). Additionally, or alternatively, at least a portion of the cell solution may be transferred (e.g., via a fluid device or a fluidic manifold) to a second cartridge.

The cell solution (e.g., cell suspension) described herein may contain cells that may be processed for subsequent use in cell therapies. The cell solution may include cells (e.g., allogeneic cells) in a fluid, such as a media (e.g., cell culture media). The cell solution may include cells from the same or different donors. Cells from the same donor may be split between one or more cartridges, such that separate cell processing steps may be performed on each of the cartridges and increase the overall throughput of the cell processing system described herein. The cell solution may be transferred to the cartridge prior to loading the cartridge into the workcell, such as by operating personnel. In some variations, the cartridge may be empty when loaded into the workcell such that the workcell may transfer a cell solution to the cartridge. In some variations, the cells from two or more cartridges may be combined according to a predetermined ratio, which may correspond to an intended therapeutic treatment for a patient.

An illustrative cell processing system for use with the automated devices, systems, and methods is shown in FIG. 1A. Shown there is a block diagram of a cell processing system 100 comprising a workcell 110 and controller 120. The workcell 110 may include one or more of an instrument 112, a robot 116 (e.g., robotic arm), a reagent vault 118, a sterile liquid transfer port 132, a sterilant source 129, a fluid source 136, a pump 138, and a sensor(s) 151. A cartridge 114 and a fluid device 142, which may be provided outside of the workcell 110 and may be used within the workcell 110, are illustrated in dashed lines. In some variations, the reagent vault 118 (or reagent vaults) may be used to store reagents, including but not limited to cell culture media, buffer, cytokines, proteins, enzymes, polynucleotides, transfection reagents, non-viral vectors, viral vectors, antibiotics, nutrients, cryoprotectants, solvents, cellular materials, and pharmaceutically acceptable excipients. Additionally, or alternatively, waste may be stored in the reagent vault 118, or within the fluid device 142 within the reagent vault 118. In some variations, waste may be store within a waste compartment of the reagent vault 118. In some variations, the fluid device 142 may be a sterile liquid transfer device (SLTD). However, it should be appreciated that the fluid device 142 may be configured to transfer any fluid (which includes liquids), whether sterile or not. The controller 120 may comprise one or more of a processor 122, a memory 124, a communication device 126, an input device 128, and a display 130.

The workcell 110 may include a fully, or at least partially, enclosed housing inside which one or more cell processing steps may be performed in a fully, or at least partially, automated process. The cartridge 114 may be moved using the robot 116 to reduce manual labor in the cell processing steps, and fluid transfers into and out of the cartridge 114 may also be performed in a fully or partially automated process, as will be described in detail herein. For example, one or more fluids may be stored in a fluid device 142, such that the one or more fluids may be transferred to the cartridge 114 and/or removed from the cartridge 114 via the fluid device 142. In some variations, the fluid device 114 may be moved within the system 100 by the robot 116. Accordingly, the workcell 110 described herein advantageously enables the transfer of fluids in an automated and metered manner for automating cell therapy manufacturing.

The workcell 110 may facilitate fluid transfers and/or cartridge transfers. For example, in some variations, the robot 116 may be configured to move more than one cartridge 114 between different bays to perform a predetermined sequence of cell processing steps (e.g., workflow). In this way, multiple cartridges 114 may be processed in parallel, as different steps of the cell processing workflow may be performed at the same time on different cartridges. In another example, a sterile liquid transfer port 132 may be coupled between two or more cartridges 114 to transfer a cell product and/or other fluid between the cartridges 114. Furthermore, the sterile liquid transfer port 132 may be coupled between any set of fluid-carrying components of the system 100 (e.g., cartridge 114, reagent vault 118, fluid source 136, fluid device 142, etc.). For example, a first sterile liquid transfer port may be coupled between a first cartridge and a corresponding sterile liquid transfer port of a fluid device.

Other suitable cell processing systems and aspects thereof are provided in, e.g., U.S. patent application Ser. No. 17/198,134, published as U.S. Patent Publication No. 2021/0283565, U.S. Patent Application No. 63/470,381, U.S. Patent Application No. 63/524,596, U.S. Patent Application No. 63/520,313, and U.S. Patent Application No. 63/520,312, each of which is incorporated in their entirety by reference herein.

1. Cartridge

The cell processing systems described herein may include one or more cartridges having one or more modules configured to interface with, or releasably couple to, one or more instruments within the workcell. Some or all of the modules may be integrated in a fixed configuration within the cartridge, though they need not be. For example, one or more of the modules may be configurable or moveable (e.g., by an operator, controller, and/or robot of the workcell) within the cartridge, permitting various formats of cartridges to be assembled. For example, the cartridge may be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module may be defined by the set of connected components that collectively perform a predetermined function. However, the components of each module may or may not be physically grouped within the cartridge. In some embodiments, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments within the workcell may interface with, or may be releasably couplable to, its respective module or modules on the cartridge in order to carry out a given cell processing step. Put another way, the workcell may include modules that interface and/or couple to a corresponding module of the cartridge. For example, a cartridge having a pump module (e.g., pump module 169 of FIG. 1B) for flowing fluid through the cartridge may be releasably couplable to a pump (e.g., pump 138 of FIG. 1A) of the workcell. One advantage of such split module/instrument designs may be to retain expensive components (e.g., motors, sensors, heaters, lasers, etc.) in the instruments of the system while less expensive components may reside in the cartridge.

Figure 1B:
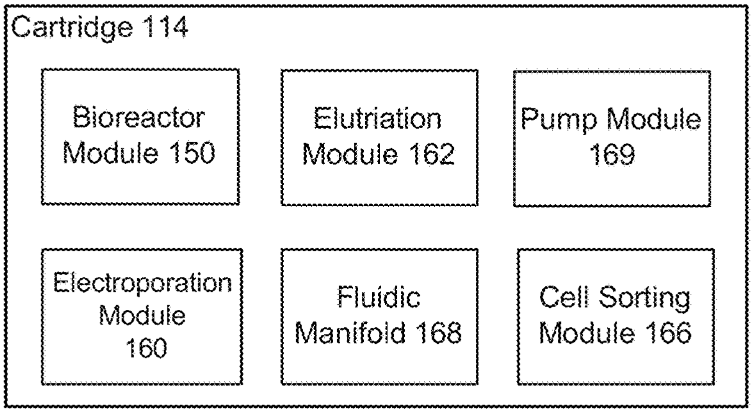
FIG. 1B is a block diagram of an illustrative variation of a cartridge that may be used with the cell processing system of FIG. 1A.

As illustrated in FIG. 1B, the cartridge 114 may be configured to contain (e.g., house) a cell solution (e.g., cell suspension) for cell processing. Any number of cell processing steps may take place upon the cells within the cartridge. Accordingly, the cartridge 114 may comprise one or more of a bioreactor module 150, an electroporation module 160, an elutriation module 162, a cell sorting module 166, a fluidic manifold 168, and a pump module 169. In some variations, the cartridge 114 may additionally or alternatively include a spinoculation module (not shown) configured to perform a spinoculation process, wherein cells of different types may be bound together. As described herein with respect to FIGS. 3A, 3D, and 4A-4D, in some variations, the cartridge may include a flow cell (e.g., flow cell 310 of FIG. 3A), which may also be referred to herein as a flow cell module. In some variations, the flow cell may be a component of another cartridge module (e.g., a module within a module). For example, in some variations, the flow cell may be a component of the cell sorting module 166.

The fluidic manifold 168 may be configured to transfer one or more fluids between one or more modules of the cartridge 114. For example, the fluidic manifold 168 may transfer a fluid from the pump module 169 to the bioreactor module 150. In another example, the fluidic manifold 168 may transfer a fluid (e.g., a cell solution) from the bioreactor module 150 to the cell sorting module 166. Further, the fluidic manifold 168 may transfer a fluid from the cell sorting module 166 to any other module. For example, as described in herein throughout, in some variations, the fluidic manifold 168 may exchange a cell solution between the bioreactor module and at least a portion of the cell sorting module 166 (e.g., the flow cell 310 of FIG. 3A) via a tube (e.g., tube 304 of FIG. 3A) coupled to the fluidic manifold 168. For performing cell separation, the cell solution may include cellular material, including target cells coupled to magnetic particles. For performing transduction, the cell solution may include cellular material and at least one transduction reagent. In another example, the fluidic manifold 168 may transfer a fluid from the cell sorting module 166 to any other module 114 after a cell sorting process has been performed. The fluidic manifold 168 may be configured to transfer the sorted cells (e.g., magnetically tagged cells) to one module and non-targeted cellular material to a different module.

The bioreactor module 150 may be configured to contain the cell solution. The bioreactor module 150 may further comprise a mixing chamber, in which the cell solution may be mixed with one or more reagents. The one or more reagents may comprise transduction reagents (e.g., a lentiviral vector and/or a virus) or magnetic particles configured to couple to cells of a specific type (e.g., target cells). The electroporation module 160 may be configured to facilitate intracellular delivery of macromolecules (i.e., transfection by electroporation). The elutriation module 162 may be configured to perform an elutriation process, wherein cellular material may be separated according to size, shape, and/or density. The pump module 169 may be configured to pump fluid in one or more directions along at least one fluid path. For example, the pump module 169 may be configured to pump a fluid to or from one or more of the elutriation module 162, the bioreactor module 150, the fluidic manifold 168, the cell sorting module 166, and any other module within the cartridge 114.

Other suitable cell processing systems and aspects thereof are provided in, e.g., U.S. patent application Ser. No. 17/198,134, published as U.S. Patent Publication No. 2021/0283565, U.S. Patent Application No. 63/470,381, U.S. Patent Application No. 63/524,596, U.S. Patent Application No. 63/520,313, and U.S. Patent Application No. 63/520,312, each of which is incorporated in their entirety by reference herein.

Figure 2B:
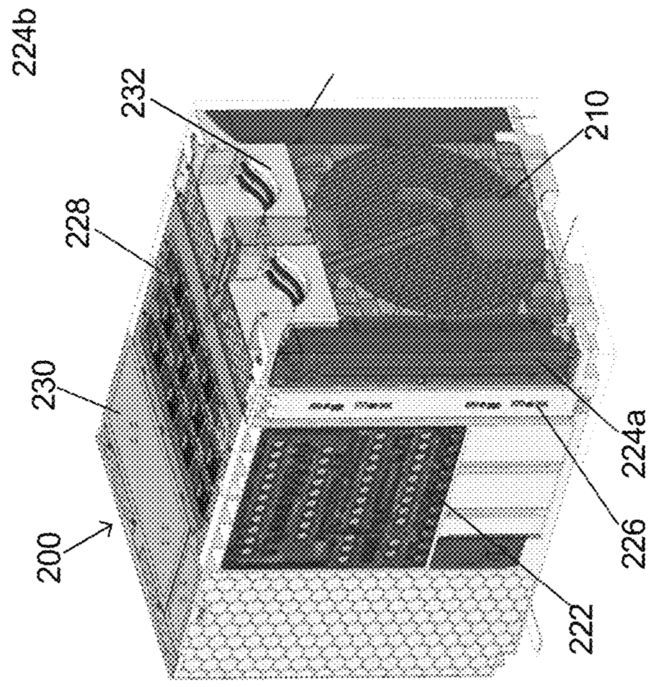
FIG. 2B is a rear perspective view of the cartridge shown in FIG. 2A.
Figure 2A:
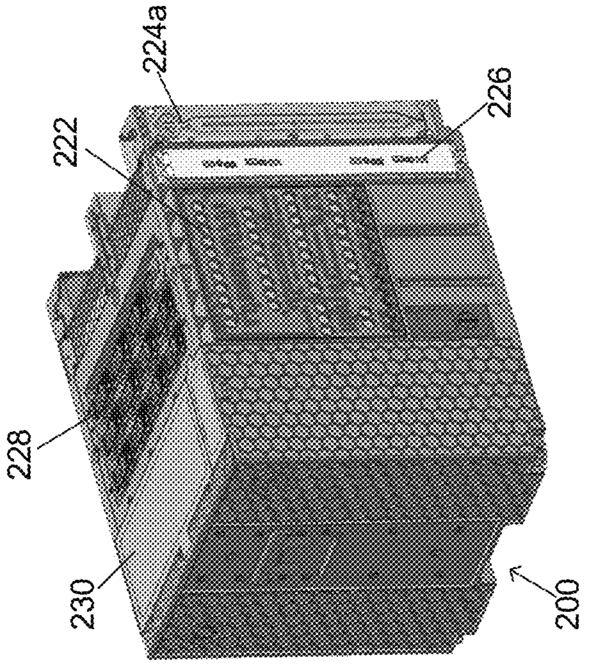
FIG. 2A is a front perspective view of an illustrative variation of a cartridge that may be provided to a cell processing system.

Referring to FIGS. 2A and 2B, an illustrative variation of a cartridge 200 is shown. The cartridge 200 may include an elutriation module 210, a fluidic manifold 222, a first cell sorting module 224*a*, a second cell sorting module 224*b*, an auxiliary module 226, a fluid device tray 228, a liquid container 230, and a pump module 232. While FIGS. 2A and 2B depict two cell sorting modules, it should be understood that any number of cell sorting modules may be used as desirable. For example, the cartridge may contain 1, 2, 3, 4, 5, more than 5, any suitable number of cell sorting modules depending on the size of the cartridge, the existence of other cell processing modules within the cartridge, and so on. Accordingly, the transduction systems described herein (e.g., transduction system 300 of FIG. 3A) may be configured to direct flow of a cell solution into and out of 1, 2, 3, 4, 5, more than 5, any suitable number of flow cells corresponding to a same number of cell sorting modules. In another aspect, the cell sorting modules 224*a*, 224*b* may perform a magnetic cell sorting process. The electroporation module 220 may be configured to facilitate intracellular delivery of macromolecules (i.e., transfection by electroporation). An electrical discharge from one or more capacitors, or current sources, may generate sufficient current in the chamber to promote transfer of a polynucleotide, protein, nucleoprotein complex, or other macromolecule into the cells in the cell product. The fluidic manifold 222 may comprise at least one fluid conduit. The at least one fluid conduit of the fluidic manifold 222 may be configured to allow fluid to pass therethrough. For example, the at least one fluid may be a liquid or a gas. In some variations, the at least one fluid may comprise a solution of cells of varying sizes and densities. The fluidic manifold 222 may include at least one fluid inlet and at least one fluid outlet, and may also include at least one valve. The fluidic manifold 222 may be fluidically connected to at least one module within the cartridge 200. For example, the fluidic manifold 222 may be configured to transfer at least one fluid to the first and/or second cell sorting modules 224*a*, 224*b* (e.g., to a flow cell of the first and/or second cell sorting modules 224*a*, 224*b* during a transduction step). The fluidic manifold 222 may be in communication with a controller, such as the controller 120 described with respect to FIG. 1A. For example, at least one valve of the fluidic manifold 222 may open and/or close in response to a command sent by the controller 120 to transfer fluid between various modules of the cartridge in accordance with a predetermined workflow.

The fluid transfer port tray 228 may include one or more ports configured to transfer fluid to or from one or more fluid devices. That is, each port of the fluid transfer port tray 228 may be configured to facilitate a sterile liquid transfer. In some variations, each port may be fluidically connected to a fluid conduit configured to fluidically couple to at least one module of the cartridge 200. For example, each port of the fluid transfer port tray 228 may be fluidically coupled to the fluidic manifold 222. In this way, a fluid may flow from a fluid device coupled to a port of the fluid transfer port tray 228 to the fluidic manifold 222, or vice versa. In some variations, each port of the fluid transfer port tray 228 may be fluidically coupled to the liquid storage container 230. The liquid storage container 230 may be configured to contain a fluid. In some variations, the fluid may be a liquid or a gas. In some variations, the liquid storage container 230 may include a plurality of liquid containers. For example, the liquid storage container 230 may include one container, two containers, three containers, or more than three containers. The liquid storage container 230 may be fluidically coupled to at least one module of the cartridge 200. In some variations, the liquid container 230 may be fluidically coupled to the fluidic manifold 222. Accordingly, a fluid may flow between a port of the fluid transfer port tray 228, the fluidic manifold 222, and the liquid storage container 230.

The cartridge may further include a pump module 232 having a pump configured to pump fluid in one or more directions along at least one fluid path. For example, the pump module 232 may be configured to pump a fluid to or from one or more of the elutriation module 210, the fluidic manifold 222, the cell sorting modules 224*a*, 224*b*, the auxiliary module 226, the fluid device tray 228, the liquid container 230, and any other module within the cartridge. The auxiliary module 226 may be configured to engage with at least one instrument and/or module. The auxiliary module 226 may include one or more electrical connectors and/or one or more fluidic connectors. In some variations, the auxiliary module 226 may be removed and replaced by any other module.

Figure 2D:
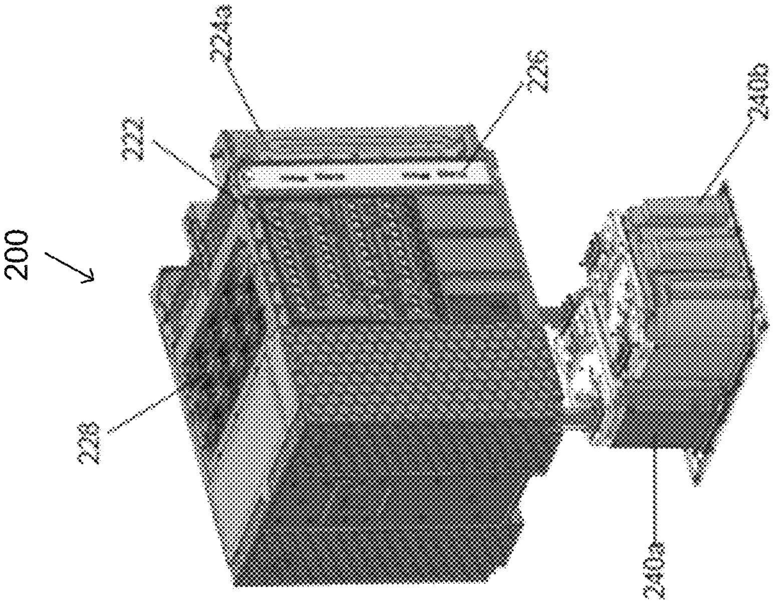
FIG. 2D is an exploded view of another illustrative variation of a cartridge.
Figure 2C:
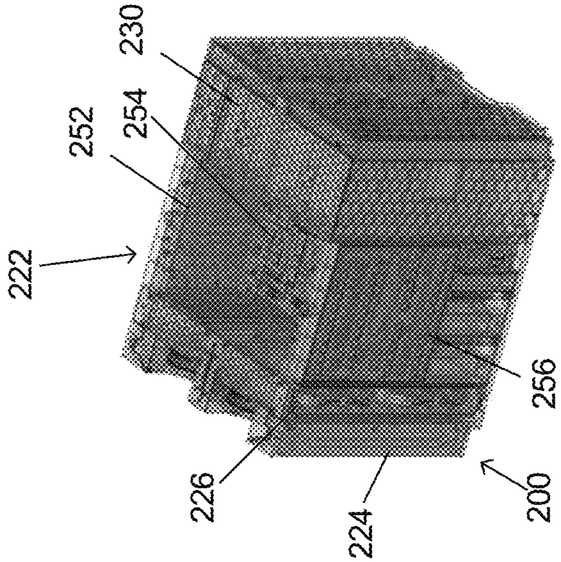
FIG. 2C is a front perspective view of another illustrative variation of a cartridge.

FIG. 2C shows an illustration variation of the cartridge 200 with the fluid device tray 228 removed. As shown, the fluidic manifold 222 may include a first end panel 252, a central panel 254, and a second end panel 256. The first end panel 252 and second end panel 256 may each define an external surface of the cartridge 200. The central panel 254 may be positioned within the cartridge 200, such that the central panel 254 may not define an external surface of the cartridge 200. The central panel 254 may extend between the first and second end panels 252, 256. That is, the central panel 254 may be coupled to each of the first and second end panels 252, 256. Accordingly, one or more fluidic pathways extend between the first and second end panels 252, 256 via the central panel 254. One or more of the first end panel, second end panel, and central panel may be fluidically coupled to one or more of the other modules of the cartridge 200, including one or more of the elutriation module 210, the cell sorting modules 224*a*, 224*b*, the auxiliary module 226, the fluid device tray 228 (of FIGS. 2A and 2B), and the liquid container 230.

FIG. 2D shows an exploded view of an illustrative variation of the cartridge 200 including a fluidic manifold 222, a first cell sorting module 224*a*, an auxiliary module 226, a fluid device tray 228, a first bioreactor module 240*a*, and a second bioreactor module 240*b*. While shown in these figures as having two cell bioreactor modules, it should be understood that any number of bioreactor modules may be used as desirable. For example, the cartridge may contain 1, 2, 3, 4, 5, more than five, or any suitable number of bioreactor modules depending on the size of the cartridge, the existence of other cell processing modules within the cartridge, and so on. Accordingly, the transduction systems described herein (e.g., transduction system 300 of FIG. 3A) may be configured to direct flow of a cell solution into and out of 1, 2, 3, 4, 5, more than 5, any suitable number of bioreactors or mixing chambers corresponding to a same number of bioreactor modules. The bioreactor modules 240*a*, 240*b* may perform a cell culturing process, as will be described in further detail below. The fluidic manifold 222 may be fluidically connected to at least one module within the cartridge 200. For example, the fluidic manifold 222 may be configured to transfer at least one fluid to the first and/or second bioreactor modules 240*a*, 240*b* (e.g., from a pump module, such as pump module 232).

Various materials may be used to construct the cartridge (including the modules thereof) and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings) and may be attached or integrated with custom components or devices. The housing of the cartridge may constitute an additional layer of enclosure that further protects the sterility of the cell product.

1.1. Transduction System

Figure 3A:
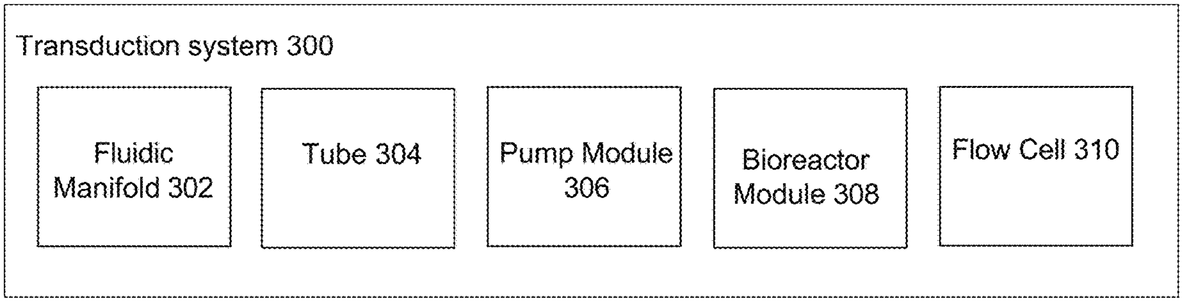
FIG. 3A is a block diagram of an illustrative variation of a transduction system of a cell processing system.

As shown in FIG. 3A, a cartridge transduction system 300 of a cell processing system (e.g., cell processing system 100) may include one or more of a fluidic manifold 302, a tube 304, a pump module 306, a bioreactor module 308, and a flow cell 310. The components of the transduction system 300 may be fluidically coupled so that cells of a cell solution may be directed to flow through the transduction system 300. For example, a fluid pathway for the cells undergoing transduction within the transduction system may move from the pump module 306 to the bioreactor module 308, then through the fluidic manifold 302 and tube 304 coupled thereto and to the flow cell 310. In some variations, the bioreactor module 308 is the starting location of the transduction system, and cells may flow from the bioreactor module 308 and through the fluidic manifold 302 and tube 304 to the flow cell 310. The fluid pathway may then be reversed such that the cells flow from the flow cell 310, back through the tube 304 and the fluidic manifold 302 coupled thereto and back to the bioreactor module 308. Indeed, the cells may be exchanged between the bioreactor module 308 and the flow cell 310 via the fluidic manifold 302 and tube 304 any number of times during the transduction step. Put another way, the tube 304, via the fluidic manifold 302, may be configured to provide bidirectional flow of a cell solution (e.g., including cells and a transduction reagent) through a cartridge (e.g., cartridge 114 of FIG. 1B) to achieve viral transduction of the cells. The tube 304, via the fluidic manifold 302, thus provides a pathway for cells to flow between the bioreactor module 308 and the flow cell 310.

Any suitable cells may be transduced using transduction system 300. Nonlimiting examples of such cells include various immune and non-immune cells such as T-cells, hematopoietic stem cells (HSCs), hematopoietic stem and progenitor cells (HSPCs), natural killer cells (NK), B cells, pre-B cells, lymphocytes, 293 cells, HEK cells, CHO cells, bacterial cells, yeast cells, any combinations thereof, and the like. In some variations, the cell solution may include cells from one or more donors. In some variations, the cells may be isolated from blood via apheresis. The cells may be suspended in a fluid (e.g., a cell culture media with one or more transduction reagents. The transduction reagents may include, for example, a lentiviral vector and/or a virus configured to introduce, for example, a chimeric antigen receptor (CAR) to cells within the cell solution. In another example, an anti-CD19 CAR-encoding lentivirus (e.g., scFv-41BB-CD3ζ, CTL019) may be introduced to target CD19+ cells. The cell solution may have a density of between about $1\times10^4$ cells/mL and about $50\times10^7$ cells/mL, such as between about $5\times10^4$ cells/mL and about $25\times10^7$ cells/mL, between about $1\times10^5$ cells/mL and about $5\times10^7$ cells/mL, or between about $5\times10^5$ cells/mL and about $2\times10^7$ cells/mL.

In some variations, the transduction system 300 may be configured to transduce cells for a time period of between about 1 minute and about 1 day, such as between about 5 minutes and about 12 hours, between about 10 minutes and about 6 hours, between about 15 minutes and about 3 hours, between about 20 minutes and about 2.5 hours, between about 25 minutes and about 2 hours, between about 30 minutes and about 1.5 hours, between about 35 minutes and about 1 hour, between about 40 minutes and about 55 minutes, or between about 45 minutes and about 50 minutes. For example, the transduction system 300 may be configured to transduce cells for about 60 minutes or about 90 minutes.

The transduction system 300 may be configured to provide successful transduction of cells using a transduction reagent such that one or more genes-of-interest of the transduction reagent may be inserted into, deleted from, or otherwise modified within the cells. A successful transduction step may be quantified via a measured or estimated viral transduction efficiency, which may equal or represent a percentage of cells that express one or more genes of the transduction reagent (e.g., a green fluorescent protein, GFP, or other visualizable protein). A successful transduction process may be defined by a transduction efficiency of about equal to or greater than 10%, 20%, 30%, 40%, or 50%, such as about equal to or greater than 55%, about equal to or greater than 60%, about equal to or greater than 65%, about equal to or greater than 70%, about equal to or greater than 75%, about equal to or greater than 80%, about equal to or greater than 85%, about equal to or greater than 90%, about equal to or greater than 95%, or about equal to or greater than 100%. In some variations, transduction efficiency may be determined using fluorescence microscopy and/or flow cytometry.

In some variations, the transduction system 300 may be configured to determine (e.g., measure and/or estimate) the transduction efficiency for a given sample of cells and to compare the transduction efficiency to a predetermined threshold (e.g., at least 50%, at least 60%, or at least 70% transduction efficiency) to inform whether the sample may proceed to a subsequent step of a cell processing workflow (e.g., cell expansion). For example, the transduction system 300 may be in communication with a controller (e.g., controller 120 of FIG. 1A), such as via a wired or wireless communication link. The transduction system 300 may transmit a signal indicative of the transduction efficiency of the sample to the controller, which may in response transmit a command to the transduction system 300 indicating that the cell processing protocol may continue, may not continue, and/or may otherwise be modified considering a comparison of the determined transduction efficiency to the predetermined threshold. In some variations, the controller may be configured to provide a notification (e.g., a visual, audible, and/or haptic notification) to an operator of the cell processing system to indicate the determined transduction efficiency and/or a status of the cell processing workflow based on the comparison of the transduction efficiency to the predetermined threshold. In some variations, the predetermined threshold may be configured to be set and/or modified by an operator (e.g., digitally configurable via a user interface of the controller).

In some variations, the transduction system 300 may include the bioreactor module 308. The bioreactor module 308 may include one or more of a bioreactor, a mixing chamber, and one or more intermediate containers (e.g., intermediate cell containers 1140, 1150, 1160 of the bioreactor module 308, and/or discrete containers including fixed volume containers, variable volume containers, and leukopak bags) configured to house a fluid (e.g., cell solution) in a stable environment. For example, depending on a volume of a given cell solution, the transduction process for the cell solution may be for one or more smaller-volume batches of the cell solution in one or more corresponding transduction subprocesses. Accordingly, given a plurality of batches of a cell solution, any transduced batches may be stored within one or more intermediate containers of the transduction system 300 while any remaining batches of the plurality of batches undergo transduction. In some variations, the volumes of each of a plurality of batches of cell suspension may be about equal. For example, each batch may have a volume of between about 0.5 mL and about 25 mL, between about 1 mL and about 15 mL, between about 6 mL and about 12 mL, or between about 8 mL and about 10 mL, including about 5 mL, about 6 mL, about 7 mL, about 8 mL, about 9 mL, about 10 mL, about 11 mL, or about 12 mL.

In some variations, one or more components of the transduction system 300 may have dimensions configured to advantageously enhance transduction efficiency or to achieve a desired transduction efficiency. For example, as described in detail with respect to Example 1 herein, it has been discovered that various surface area to volume ratios of one or both of the tube 304 and the flow cell 310 may impact the transduction efficiency of the sample flowing through the transduction system 300. In particular, a surface area to volume ratio of the tube 304 and/or the flow cell 310 of between about 400 $mm^2$/mL and about 6,000 $mm^2$/mL, such as between about 1,260 $mm^2$/mL and about 5,080 $mm^2$/mL, may result in a transduction efficiency that is greater than 10% of that of a static transduction process (where remaining variables like density of the cell solution, time period for transduction, type of transduction reagent, etc., may be constant).

In some variations, one or more components of the transduction system 300 may be operatively coupled via, for example, a controller (e.g., the controller 120 of FIG. 1A). That is, one or more components of the transduction system 300 may share information (e.g., sensor data) via a common controller configured to actuate the transduction system according to the shared information. Moreover, while the transduction system 300 may be described herein as including one or more of one or more of the fluidic manifold 302, the tube 304, the pump module 306, the bioreactor module 308, and the flow cell 310, it should be understood that other components of the cell processing systems herein may additionally or alternatively contribute to the transduction system 300.

1.1.1. Fluidic Manifold

In order for fluid to move between the various modules of the cartridge and through the transduction system 300, the cartridges described herein may include the fluidic manifold 302. The cell processing steps described herein, such as transduction, may each require one or more fluids (e.g., a cell suspension, a media, a buffer, a reagent). The one or more fluids may be provided to one or more modules of a cartridge of the workcell according to a pre-defined workflow. Accordingly, one or more fluids may flow through the fluidic manifold 302 of the cartridge, such that the fluidic manifold 302 may control one or more of the type, quantity, flow rate, timing, and destination of any fluid flowing therethrough. That is, the fluidic manifold may be connected to the one or more modules of the cartridge by one or more fluid conduits (e.g., tubes or channels, such as tube 304 described below).

In some variations, the pre-defined workflow may be programmed into a controller of a cell processing system (e.g., system 100 of FIGS. 1A and 1B) as described herein throughout. For example, the fluidic manifold may be controlled to deliver a fluid to the cartridge modules in a pre-defined sequence according to a workflow, or may bypass one or more modules altogether using one or more valves. The fluidic manifold 302 may be fluidically coupled to multiple fluid devices used to provide solutions or reagents, store cell products, or to collect waste solutions or reagents. The fluid may be a liquid or a gas. In some variations, the fluid may be a solution (e.g., a cell solution, a cell suspension). For example, the solution may comprise one or more of a cell, a media, a buffer, and a reagent (e.g., an activation reagent or a transduction reagent).

The fluidic manifold 302 may be used to facilitate one or more cell processing steps, such as one or more of cell activation, transduction, and expansion. In some variations, an activating step, such as a T-cell activation step or an NK-cell activation step, may comprise activating a selected population of cells in the solution by conveying an activating reagent via the fluidic manifold 302 to a module (e.g., the bioreactor model 308) containing the cell solution. In some variations, a transduction step may include transducing a selected population of cells in the solution by conveying an effective amount of a viral vector, via the fluidic manifold 302, to a module (e.g., the bioreactor module) containing the cell solution. Multiple vectors may be used in a single transduction step. The vector may be delivered with one or more proteins (e.g., a protein delivered in a liposome or a lipid nanoparticle) or using a cell penetrating peptide. Further, the transduction step may include modifying cells by inserting, deleting, or mutating one or more polynucleotides in the cell (e.g., the genome of the cell, or any other polynucleotide in the cell). In some variations, an expansion step may comprise expanding the cells in the solution by conveying the solution to the bioreactor module 308 via the fluidic manifold 302, operating the robot to move the cartridge to the bioreactor instrument (e.g., bioreactor docking station module configured to engage with the bioreactor module 308) so that the bioreactor instrument interfaces with the bioreactor module 308, and operating the bioreactor instrument to cause the bioreactor module 308 to allow the cells to expand by cellular replication. The bioreactor instrument may provide closed-loop control of one or more of temperature, dissolved oxygen concentration, acidity (pH), and mixing intensity for the bioreactor.

In some variations, the fluidic manifold 302 may be used to facilitate a static cell processing step, which may be configured to maintain a fluid in an unagitated state. For example, the unagitated state may be associated with maintaining a fluid in a fluid device without stirring the fluid, such as with an impeller. In contrast, an agitated state may be associated with stirring the fluid via the impeller. In another example, the static step may comprise conveying the solution to a bioreactor module of the cartridge via the fluidic manifold, operating the robot to move the cartridge to the bioreactor instrument so that the bioreactor module may interface with the bioreactor instrument, and operating the bioreactor instrument to cause the bioreactor module to maintain the cells.

In some variations, the fluidic manifold may be used more than once in a method of cell processing. For example, during a transduction step, the fluidic manifold may be used to transfer a cell solution through the tube and between the bioreactor module and the flow cell any suitable number of times.

Figure 3B:
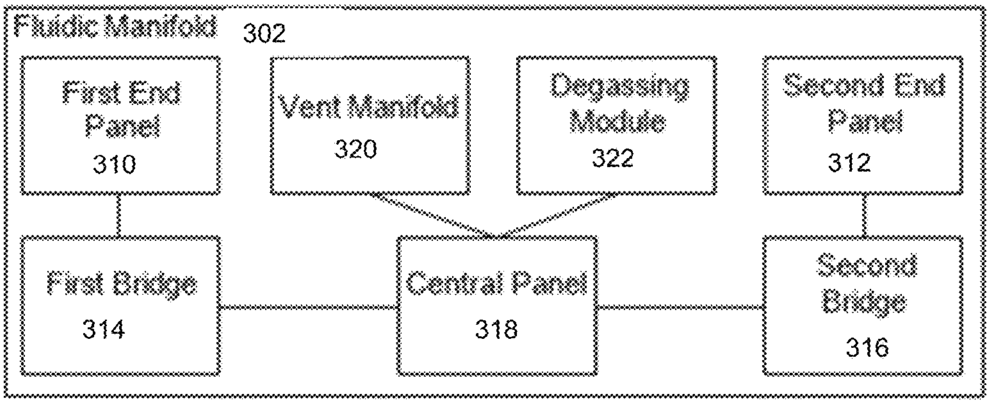
FIG. 3B is a block diagram of an illustrative variation of a fluidic manifold of the transduction system of FIG. 3A.
Figure 3C:
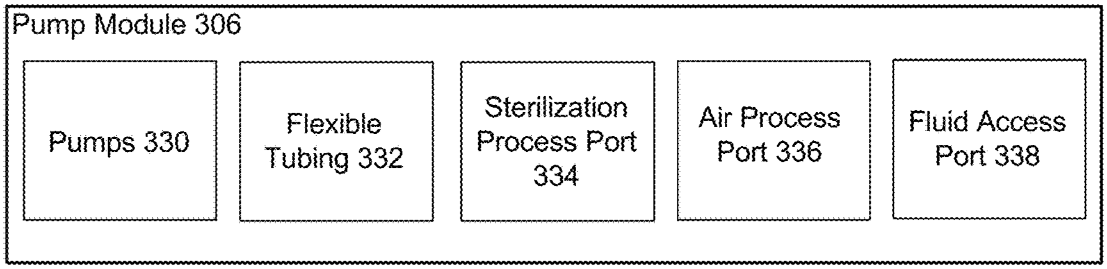
FIG. 3C is a block diagram of an illustrative variation of a pump module of the transduction system of FIG. 3A.

Referring to FIG. 3B, a block diagram of an exemplary variation of the fluidic manifold 302 is shown. The fluidic manifold 302 may comprise a first end panel 310, a second end panel 312, a first bridge 314, a second bridge 316, a central panel 318, a vent manifold 320, and a degassing module 322. The first and second end panels 310, 312 may be coupled to the central panel 318 by the first and second bridges 314, 316. That is, the first end panel 310 may be coupled to the first bridge 314, which may also be coupled to the central panel 318. Similarly, the second end panel 312 may be coupled to the second bridge 316, which may also be coupled to the central panel 318. The end panels 310, 312 may be coupled to the respective bridges 314, 316 by a mechanical fastener (e.g., screws, nails, bolts), an adhesive (e.g., glue), a friction fit (e.g., a protrusion of one component received within a corresponding opening of another component, such as a fluid conduit), or a combination thereof.

One or more components of the fluidic manifold may be fluidically connected. For example, the first end panel 310 may be fluidically connected to the central panel 318 via the first bridge 314. That is, the first end panel 314 may comprise a fluidic pathway that is fluidically connected to a fluidic pathway of the first bridge 314, which, in turn, may be fluidically connected to a fluidic pathway of the central panel 318. Similarly, the second end panel 312 may be fluidically connected to the central panel 318 via the second bridge 316. That is, the second end panel 312 may comprise a fluidic pathway that is fluidically connected to a fluidic pathway of the second bridge 316, which, in turn, may be fluidically connected to a fluidic pathway of the central panel 318. In some variations, the first end panel 310 may be directly fluidically connected to the central panel 318, such that a fluidic connection therebetween may bypass the first bridge 314. Additionally, or alternatively, the second end panel 312 may be directly fluidically connected to the central panel 318, such that a fluidic connection therebetween may bypass the second bridge 316. The central panel 318 may be fluidically connected to one or more of the vent manifold 320 and degassing module 322. For example, a fluidic pathway of vent manifold 320 may be fluidically connected to a fluidic pathway of the central panel 318. Additionally, or alternatively, a fluidic pathway of degassing module 322 may be fluidically connected to a fluidic pathway of the central panel 318. In some variations, a fluidic pathway of the first and/or second end panel 310, 312 may be fluidically connected to the vent manifold 320 and/or degassing module 322.

1.1.2. Tube

The tube 304 may be a fluidic tube configured to provide a pathway for cells (e.g., of a cell solution) to flow back and forth between the bioreactor module 308 and the flow cell 310. For example, the tube 304 may include a first end coupled to the fluidic manifold 304 and a second end coupled to the flow cell 310, and the fluidic manifold 302 may be coupled to the bioreactor module 308 (as described herein) such that cells may be transferred from the bioreactor module 308 to the flow cell 310 via the tube 304. In some variations, the tube may include one or more tubes, such as at least one tube, or a plurality of tubes (e.g., 2, 3, 4, 5, 6, 7, 8, 9, 10, 15, 20, or any suitable number of tubes). As described in more detail herein, in some variations, the tube 304 may include a first tube configured to fluidically couple to an inlet port of the flow cell 310 and a second tube configured to couple to an outlet port of the flow cell 310. In some variations, the tube 304 may further include a third tube configured to fluidically couple to a second outlet port of the flow cell 310. In some variations, the tube 304 may be a component of the fluidic manifold 302.

As discussed above and in more detail with respect to Example 1 herein, one or more dimensions of the tube 304 may be configured to assist in achieving a desired transduction efficiency. For example, it has been found that a surface area to volume ratio of the tube 304 of between about 400 $mm^2/mL$ and about 7,000 $mm^2/mL$ (e.g., between about 500 $mm^2/mL$ and about 6,000 $mm^2/mL$, between about 1,000 $mm^2/mL$ and about 5,500 $mm^2/mL$, between about 1,100 $mm^2/mL$ and about 5,250 $mm^2/mL$, between about 1,200 $mm^2/mL$ and about 5,000 $mm^2/mL$, between about 1,300 $mm^2/mL$ and about 4,500 $mm^2/mL$, between about 1,400 $mm^2/mL$ and about 4,000 $mm^2/mL$, or between about 1,500 $mm^2/mL$ and about 3,000 $mm^2/mL$) may enable successful transduction (e.g., greater than about 50%, greater than about 60%, greater than about 70%, etc., as described above) of a sample via the transduction system 300. In some variations, the surface area to volume ratio of the tube 304 may be between about 1,260 $mm^2/mL$ and about 5,080 $mm^2/mL$, which may increase the probability of the transduction reagent contacting the cells without causing the cells to collide into each other excessively when flowing through the transduction system 300.

The tube 304 may have a width or diameter (e.g., inner width or inner diameter in the case of a tube having a circular cross-section) of between about 1 mm and about 20 mm, such as between about 1.25 mm and about 15 mm, between about 1.5 mm and about 10 mm, between about 1.75 mm and about 5 mm, between about 2 mm and about 4 mm, or between about 2.5 mm and about 3.5 mm. For example, the width or diameter of the tube 304 may be between about 1.5 mm and about 3.5 mm, such as between about 1.57 mm and about 3.18 mm. The tube 304 may have circular, oval, square, or rectangular cross-sectional shape. In some variations, a circular tube 304 may have a diameter of between about 1 mm and about 10 mm. In some variations, an oval tube 304 may have a first diameter of between about 1 mm and about 10 mm, and a second diameter of between about 1 mm and about 30 mm. In some variations, a square tube 304 may have a width of between about 1 mm and about 10 mm. In some variations, a rectangular tube 304 may have a first width of between about 1 mm and about 10 mm, and a second width of between about 1 mm and about 30 mm. Each of the diameter of the circular tube, the first diameter of the oval tube, the width of the square tube, and the first width of the rectangular tube may have a diameter or width, respectively, of between about 1.5 mm and about 3.5 mm, such as between about 1.57 mm and about 3.18 mm.

The tube 304 may have a length of between about 10 mm and about 5,000 mm, such as between about 25 mm and about 2,500 mm, between about 50 mm and about 1,000 mm, between about 100 mm and about 750 mm, between about 150 mm and about 500 mm, or between about 200 mm and about 250 mm. Moreover, the tube 304 may have a surface area (e.g., an internal surface area of the length of the tube 304) of between about 1 $mm^2$ and about 50 $mm^2$, such as between about 3 $mm^2$ and about 40 $mm^2$, between about 5 $mm^2$ and about 30 $mm^2$, between about 7 $mm^2$ and about 20 $mm^2$, between about 9 $mm^2$ and about 18 $mm^2$, between about 10 $mm^2$ and about 17 $mm^2$, between about 11 $mm^2$ and about 16 $mm^2$, between about 12 $mm^2$ and about 15 $mm^2$, or between about 13 $mm^2$ and about 14 $mm^2$. Further, the tube 304 may define a volume (e.g., a volume of a lumen along the length of the tube 304) of between about 1 μL and about 250 μL, such as between about 2 μL and about 100 μL, between about 4 μL and about 80 μL, between about 8 μL and about 60 μL, between about 10 μL and about 40 μL, between about 12 μL and about 20 μL, or between about 14 μL and about 18 μL. In variations where the transduction system 300 may include a plurality of tubes, each of the plurality of tubes may have one or more unique dimensions. In some variations, each of the plurality of tubes may have one or more identical dimensions.

The tube 304 may generally be flexible. Accordingly, the tube 304 may be made of one or more flexible materials such as various rubbers and plastics.

1.1.3. Pump Module

Figure 3D:
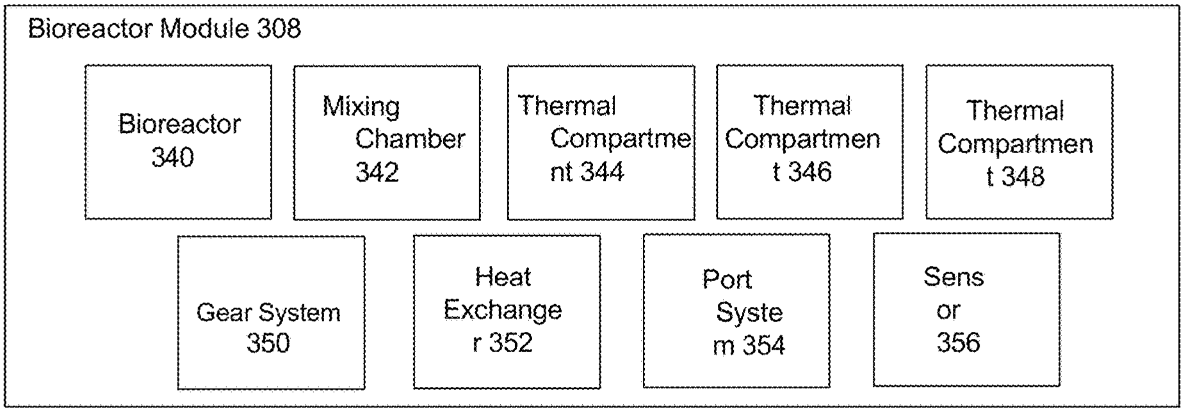
FIG. 3D is a block diagram of an illustrative variation of a bioreactor module of the transduction system of FIG. 3A.

To enable fluid (e.g., gas and/or liquid) flow throughout the cell processing systems described herein, a cartridge may include the pump module 306. Referring to FIG. 3D, a block diagram of an illustrative variation of a pump module 306 of the transduction system 300 of FIG. 3A is shown. The pump module 306 may include one or more pumps 330 fluidically connected to the fluidic manifold 302. The one or more pumps 330 may include a direct lift pump, displacement pump, gravity pump, reciprocating pump, rotary pump, a peristaltic pump, or combinations thereof. The pump module 306 may also be configured to releasably couple to a workcell pump (e.g., pump 138 of FIG. 1A). The workcell pump may be configured to engage compressible fluidic tubing of the pump module 306 of a fluid device to transfer the fluid between the fluid device and the cartridge. In some variations, the actuator may be a pneumatic actuator and the pump can be a peristaltic pump. In some embodiments, one or more of the instruments of the system may include one or more integrated pump actuators to permit the system to convey fluid between modules, fluidic containers, or other components while the cartridge may be interfaced to that module. The system (e.g., workcell) may also include a dedicated pump instrument (e.g., a pump docking station module) configured to interface with at least one of the one or more pumps of the pump module 306.

The pump module 306 may also include compressible fluidic tubing 332, and a plurality of ports including sterilization process port(s) 334, one or more air process ports 336, and a fluid access port 338.

With respect to transduction, the pump module 306 may be configured to supply the bioreactor module 308 with fluid for a cell suspension prior to flowing the cell suspension throughout the transduction system 300. Further, in some variations, the pump module 306 may be configured to maintain a constant flow rate of cells (e.g., the cell solution) through the tube 304. For example, the pump module 306 may maintain the flow rate between about 1 mL/min and about 150 mL/min, about 2 mL/min and about 125 mL/min, about 3 mL/min and about 100 mL/min, about 4 mL/min and about 75 mL/min, about 5 mL/min and about 50 mL/min, about 6 mL/min and about 25 mL/min, about 7 mL/min and about 15 mL/min, or about 8 mL/min and about 10 mL/min. In some variations, the flow rate may be about 1 mL/min, about 2 mL/min, about 3 mL/min, about 4 mL/min, about 5 mL/min, about 6 mL/min, about 7 mL/min, about 8 mL/min, about 9 mL/min, about 10 mL/min, about 15 mL/min, about 20 mL/min, about 25 mL/min, about 30 mL/min, about 35 mL/min, about 40 mL/min, about 45 mL/min, or about 50 mL/min. Similarly, in some variations, the flow rate may be at least 1 mL/min, at least 2 mL/min, at least 3 mL/min, at least 4 mL/min, at least 5 mL/min, at least 6 mL/min, at least 7 mL/min, at least 8 mL/min, at least 9 mL/min, or at least 10 mL/min. In some variations, the flow rate may be at least 8.6 mL/min (i.e., at least 8600 L/min), such as about 8.683 mL/min (i.e., 8683 μL/min). Moreover, in some variations, the pump module 306 may additionally or alternatively be configured to vary the flow rate of the cell solution within the transduction system 300.

1.1.4. Bioreactor Module

The bioreactor module 308 may perform one or more cell processing steps associated with cell culturing. For example, the bioreactor module 308 may be configured to perform at least a portion of one or more of an activating step, a transduction step, and an expansion step, a transfection step, a perfusion step, a depletion step, and a seeding step.

An activating step, such as a T-cell activation step or an NK-cell activation step, may include activating cells of a cell solution within the bioreactor module 308 upon receiving an activating reagent (e.g., via the fluidic manifold 302) within a suitable component of the bioreactor module 308, such as either of the bioreactor or the mixing chamber of the bioreactor module 308 described in detail herein.

As described above, in the transduction step, a transduction reagent (e.g., a lentiviral vector and/or a virus) may be introduced to a cell solution within the bioreactor module 308 (e.g., within a bioreactor or mixing chamber of the bioreactor module 308). Like the activating step, in some variations, the bioreactor module 308 may receive the transduction agent from the fluidic manifold 302. Subsequently, the cell solution may be flowed from the bioreactor module 308 to the flow cell 310 via the fluidic manifold 302 and tube 304 (and exchanged between the bioreactor module 308 and the flow cell 310 any number of times) in order to achieve a desired transduction efficiency of the transduction reagent into the cells of the cell solution.

In an expansion step, the number of cells within a cell solution may be increased. For example, the bioreactor module 308 may comprise an impeller configured to mix the cell solution contained therein. The rate of rotation of the impeller may be adjusted to increase or decrease the efficacy of the mixing. For example, increasing the rate of rotation may correspond to a greater increase in the number of cells. Conversely, decreasing the rate of rotation may correspond to a lower increase in the number of cells. Cell expansion may be performed for a pre-determined duration (e.g., between about 5 days and about 7 days) which may correspond to a target cell count. For example, a relatively low target cell count may correspond to a relatively short pre-determined duration (e.g., about 30 minutes up to about 72 hours), and a relatively high target cell count may correspond to a relatively long pre-determined duration (e.g., about 72 hours to about 14 days). The bioreactor instrument may provide closed loop control of temperature, dissolved oxygen, and/or acidity (pH) to the bioreactor to permit growth of the cells intended for culturing (e.g., white blood cells). Optionally, one or more reagents may be introduced to the bioreactor, for example, cell-type specific activating reagents.

In a transfection step, a transfection reagent (e.g., a nucleic acid) may be introduced to a cell solution by a nonviral method. Transfection may be configured to knockout certain cell types that may be associated with eliciting immune responses (e.g., graft vs host disease) in subsequent patients. That is, transfection may decrease the likelihood that a cell therapy recipient rejects the cells developed by the cell processing described herein. Transfection may be performed by adding one more transfection reagents to the bioreactor module containing the cell solution, such that the cells may be modified by the transfection reagents. The transfection reagent may comprise a liquid nanoparticle (LNP).

In a perfusion step, a pre-determined volume of media within the cell solution contained within the bioreactor of the bioreactor module may be replaced. Perfusion may be useful in maintaining an amount of nutrients in the cell solution associated with a desired cell growth rate and/or maintain a suitable pH level. For example, cells may consume glucose and/or oxygen dissolved in the cell solution during the cell growth process, so a low level of glucose and/or dissolved oxygen may reduce or prevent cell growth. Conversely, cells may expel (e.g., excrete) lactate and/or carbon dioxide during the cell growth process, so an excess of lactate and/or carbon dioxide may inhibit cell growth by displacing glucose and/or dissolved oxygen. Accordingly, the perfusion process may ensure the amount of glucose and/or dissolved oxygen within the cell solution remains above a level sufficient to support the desired cell growth and/or the amount of lactate and/or carbon dioxide within the cell solution remains below a level sufficient to prevent inhibiting cell growth. In addition, in some variations, the cell culturing process may be optimally performed within a target pH range. For example, the target pH range may be between about 7 and about 7.6, about 7.1 and about 7.5, or about 7.2 and about 7.4. In some variations, the target pH may about 7, about 7.1, about 7.2, about 7.3, about 7.4, about 7.5, or about 7.6. The cell growth and/or division processes may result in carbon dioxide, which may form bicarbonate ions and hydrogen ions. The latter of which may decrease the pH of the cell solution. Accordingly, perfusion may remove a volume of the cell solution such that new cell solution may be added without overfilling the bioreactor module. In some variations, perfusion may be performed continuously such that a volume of media may be constantly being removed and new (e.g., fresh) media may be constantly being added. Cells within the cell solution may be retained within the bioreactor (e.g., via a filter), such that only the media may be exchanged. In some variations, the pre-determined volume of media exchanged (e.g., removed and replaced) may be about 10% to about 100%, including about 25%, about 50%, and about 75% of the original cell solution. In some variations, perfusion may be performed within a first bioreactor module of the cartridge. In other variations, at least a portion of the cell solution may be transferred to a second bioreactor module, such that perfusion may be performed in the second bioreactor module.

In a depletion step, unmodified cells of the cell solution may be removed from the cell solution. Cell depletion may be configured to separate cells within a cell solution using one or more depletion reagents. For example, the depletion reagents (e.g., depletion microbeads) may be added to the cell solution, which may be stored in the bioreactor module, such that the cells may be incubated with the depletion reagents. That is, the depletion reagents may be configured to bind to certain cells (e.g., target cells), which may mark the non-bonded cells for subsequent removal. In an exemplary variation, the depletion reagents may bind to CD3+ cells (which may include CD4+ and CD8+ cells) such that the bounded CD3+ may be separated from unmodified T cells. Accordingly, the unmodified T cells may be removed from the cell solution.

In a seeding step, cells that have previously undergone one or more cell processing steps may be used to begin a new cell culturing process. For example, a portion of a cell solution from a first bioreactor module may be transferred to a second bioreactor module. The cell culturing process may be performed in the second bioreactor module. The seeding step may facilitate a faster and/or successful cell culturing process.

Further, the bioreactor module 308 may be configured to facilitate one or more measurements. For example, one or more of the bioreactor, thermal compartments, and mixing chamber of the bioreactor module 308 may have a window configured for optical detection. That is, a sensor may be operatively coupled to the one or more windows such that one or more parameters within the bioreactor module may be measured. Additionally, or alternatively, the bioreactor module may comprise one or more fluid conduits configured to sample a portion of the fluid within the bioreactor module. For example, the cartridge may comprise one or more sensors configured to measure one or more of a lactate value and a glucose value of the sample. Thus, the one or more sensors may comprise a glucose sensor and/or a lactate sensor. Advantageously, measuring one or more of a lactate value and a glucose value within the cartridge may increase the efficiency of the cell processing described herein by reducing the time and/or steps required to obtain a lactate and/or glucose measurements. In other words, the sample may be measured within the cartridge and thus avoid additional steps associated with transferring the sample to an analytical instrument. In another example, the portion of the fluid within one or more of the bioreactor and mixing chamber may be removed via the fluid conduit and transferred to an analytical instrument. The analytical instrument may be within the workcell (e.g., an online instrument) or, in some variations, may be outside of the workcell (e.g., an offline instrument). The analytical instrument may be configured to measure one or more a lactate value and a glucose value of the sample. The flexibility provided by the analytical instrument may facilitate higher throughput by the bioreactor module described herein, as more than one measurement may be performed in parallel without interrupting the cell culturing process.

In some variations, a single bioreactor instrument may interface with one or more bioreactors (e.g., multiple bioreactors of the same size or different size). Additionally, or alternatively, in some variations, each of the plurality of bioreactor instruments may interface with each of a plurality of corresponding bioreactors. In some variations, the bioreactor instrument may be designed to interface with several cartridges simultaneously.

Referring to FIG. 3D, a block diagram of an exemplary variation of the bioreactor module 150 is shown. The bioreactor module 308 may comprise a bioreactor 340, a mixing chamber 342, a first thermal compartment 344, a second thermal compartment 346, a third thermal compartment 348, a gear system 350, a sensor 356, a heat exchanger 352, and a port system 354. The bioreactor 340, mixing chamber 342, first thermal compartment 344, second thermal compartment 346, and third thermal compartment 348 may be fluidically and/or thermally connected. For example, a fluid may be transferred between one or more of the bioreactor 340, mixing chamber 342, first thermal compartment 344, second thermal compartment 346, and third thermal compartment 348. In another example, a heat exchanger may be coupled to one or more the bioreactor 340, mixing chamber 342, first thermal compartment 344, second thermal compartment 346, and third thermal compartment 348, such that a thermal environment may be maintained throughout the bioreactor module 308.

In some variations, the bioreactor 340, mixing chamber 342, first thermal compartment 344, second thermal compartment 346, and third thermal compartment 348 may be positioned within the bioreactor module 150 in any configuration. For example, the first thermal compartment 344 may be positioned adjacent the bioreactor and/or the second thermal compartment 346 may be positioned adjacent the bioreactor. In some variations, the first thermal compartment 344 and the second thermal compartment 346 may interlock with one another. That is, the first thermal compartment 344 and the second thermal compartment 346 may have shapes that correspond to each other. For example, one or more sidewalls of the first thermal compartment 344 may include one or more bends, and one or more sidewalls of the second thermal compartment 346 may include one or more bends that mirror the one or more bends of the first thermal compartment 344. In some variations, the first thermal compartment 344 and the second thermal compartment 346 may share a sidewall, such that fluid within the first thermal compartment 344 may be on a first side of the shared sidewall and fluid the second thermal compartment 346 may be on the second side of the shared sidewall. The configuration described herein may facilitate heat transfer, such that a thermal environment within the bioreactor module may be relatively even throughout. Maintaining a relatively even thermal environment may avoid issues associated with cells experiencing sudden changes in temperature, which may otherwise inhibit, slow down, or stop cell culturing and/or growth. That is, the cells should ideally be maintained at a constant temperature as the cells are transferred between the components of the bioreactor module 308.

The bioreactor 340 may be configured to hold a volume of fluid and perform one or more processes to the fluid therein. For example, the bioreactor 340 may be configured to perform at least a portion of a transduction process described herein. Accordingly, the bioreactor 340 may advantageously facilitate high-throughput cell processing by performing one or more processes within the bioreactor 340 itself and thereby reducing or eliminating the need to transfer the fluid to another module. The one or more processes and/or fluid transfers in and/or out of the bioreactor 340 may be performed in accordance with a predetermined workflow. In some variations, the bioreactor 340 may comprise one or more sidewalls that may be impermeable to liquid and/or gas. The bioreactor 340 may be configured to hold a volume of fluid between about 5 mL to about 2 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, about 1 L, about 1.5 L, or about 2 L. The bioreactor 340 may comprise a cross-sectional shape such as a circle, an oval, a rectangle, a triangle, or a combination thereof.

The mixing chamber 342 may be configured to hold a volume of fluid and perform one or more processes to the fluid therein. For example, the mixing chamber 342 may be configured to perform a stirring process. That is, the mixing chamber 342 may receive one or more reagents, which may be combined with a fluid using an impeller of the mixing chamber 342. The impeller may rotate such that the one or more reagents may mix with (e.g., contact) target cells (e.g., cells intended for further processing and/or use in cell therapies). The resulting mixture may be transferred out of the mixing chamber 342 to the bioreactor 340, thermal compartments 344, 346, 348 and/or another module of the cartridge (e.g., cartridge 114 of FIG. 1B). The fluid and/or reagent(s) may be transferred in and/or out of the mixing chamber 342 in accordance with a pre-determined workflow. For example, the mixing chamber 342 may comprise one or more sidewalls that may be impermeable to liquid and/or gas. The mixing chamber 342 may be configured to hold a volume of fluid between about 5 mL to about 1 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, or about 1 L. The mixing chamber 342 may comprise a cross-sectional shape such as a circle, an oval, a rectangle, a triangle, or a combination thereof.

The thermal compartments 344, 346, 348 may each be configured to hold a volume of fluid in a stable environment. For example, one or more the thermal compartments 344, 346, 348 1160 may be thermally coupled to the bioreactor 340 and/or mixing chamber 342, such that there be thermal equilibrium therebetween. The thermally balanced configuration may facilitate cell culturing by mitigating issues associated with a cell solution experiencing changes in temperature. For example, cell growth and/or division may slow down or stop completely if the cell solution temperature drops below an intended value. In another example, one or more cell proteins may denature if the cell solution temperature increases above an intended value.

Further, in some variations, the thermal compartments 344, 346, 348 may be referred to as intermediate cell containers, cell hotels, or compartments where the thermal compartments 344, 346, 348 may be configured to house a fluid (e.g., cell solution) in a stable environment. For example, during a transduction step including transduction sub-steps for each of a plurality of batches of a cell solution, transduced batches may be stored within any one of, or a combination of, intermediate cell containers 344, 346, 348 while any remaining batches of the plurality of batches undergo transduction.

Additionally, or alternatively, the thermal compartments 344, 346, 348 may maintain a stable gaseous environment therein. That is, one or more the thermal compartments 344, 346, 348 be fluidically connected to the port system 354, which may be configured to provide oxygen, carbon dioxide, nitrogen, and/or sterile air as required to maintain the cell solution at a stable pH and with sufficient oxygen and/or nitrogen dissolved therein. Accordingly, the thermal compartments 344, 346, 348 may be configured to facilitate cell culturing by maintaining a thermal and/or gaseous environment. In some variations, each of the thermal compartments 344, 346, 348 may comprise one or more sidewalls that may be impermeable to liquid and/or gas. Each of the thermal compartments 344, 346, 348 may be configured to hold a volume of fluid between about 5 mL to about 1 L, about 50 mL to about 800 mL, or about 100 mL to about 600 mL, including about 50 mL, about 100 mL, about 200 mL, about 300 mL, about 400 mL, about 500 mL, about 600 mL, about 700 mL, about 800 mL, about 900 mL, or about 1 L. In some variations, the thermal compartments 344, 346, 348 may be configured to hold the same volume of fluid, but they need not be configured to do so. For example, the first thermal compartment 344 may be configured to hold a volume of about 600 mL, the second thermal compartment 346 may be configured to hold a volume of about 100 mL, and the third thermal compartment 348 may be configured to hold a volume of about 600 mL. The volume(s) may be determined by a pre-determined workflow. For example, after a cell sorting step, cellular material may be transferred to the second thermal compartment 346. The relatively smaller volume of the second thermal compartment 346 may correspond to the relatively small number of cells that may be obtained via the cell sorting step described previously. In another example, the 600 mL capacity of the first and third thermal compartments 344, 348 may be appropriate to house cellular material after performing an expansion step, which may correspond to a relatively high number of cells. The fluid may be transferred in and/or out of each of the thermal compartments 344, 346, 348 in accordance with a pre-determined workflow.

The heat exchanger 352 may be configured to maintain a thermal environment within the bioreactor module 150. The heat exchanger 352 may be thermally connected to one or more of the bioreactor 340, mixing chamber 342, first thermal compartment 344, second thermal compartment 346, and third thermal compartment 348. For example, the heat exchanger 352 may be configured to generate an amount of heat and/or remove an amount of heat from a component within the bioreactor module. The thermal connection may be facilitated by one or more thermal paths. The thermal path(s) may be defined by a thermal conduit and/or a thermal pad. The thermal paths (e.g., thermal conduits, thermal pads) may comprise a thermally conductive material. For example, the thermally conductive material may be a metal (e.g., copper, aluminum). In some variations, a thermal pad may be underneath one or more of the bioreactor 340, mixing chamber 342, first thermal compartment 344, second thermal compartment 346, and third thermal compartment 348. The thermal pads may be substantially flat, such that the thermal pads may couple with a corresponding flat surface of the bioreactor 340, mixing chamber 342, first thermal compartment 344, second thermal compartment 346, and/or third thermal compartment 348. A thermal conduit may connect one or more of the thermal pads underneath one or more of the bioreactor 340, mixing chamber 342, first thermal compartment 344, second thermal compartment 346, and third thermal compartment 348. The heat exchanger 352 may be controlled by a controller, such as the controller 120 of FIG. 1A. For example, the controller 120 may control the amount of heat generated and/or removed by the heat exchanger 352 by increasing and/or decreasing an electrical current provided to the heat exchanger 352. Accordingly, the heat exchanger 352 may control the thermal environment throughout the bioreactor module 308.

The sensor 356 may be configured to measure one or more parameters of the bioreactor module 150. For example, the sensor 356 may be operatively coupled to the bioreactor 340, mixing chamber 342, and/or thermal compartments 344, 346, 348. The sensor 356 may be configured to measure temperature, pressure, gas concentration, humidity, pH, fluid level, and/or dissolved oxygen. For example, the sensor 356 may be operatively coupled to a window of the bioreactor 340, such that the sensor 356 may measure a pH and/or dissolved oxygen value of a fluid within the bioreactor 340. In another example, the sensor 356 may measure a gas concentration (e.g., unit of gas per unit of volume) of oxygen, nitrogen, and/or carbon dioxide within one or more bioreactor 340, mixing chamber 342, and/or thermal compartments 344, 346, 348. The sensor 356 may be in communication with a controller, such as the controller 120. Accordingly, the sensor 356 may facilitate a closed-loop system by providing one or more measurements to the controller 120 which may, in response, adjust one or more parameters (e.g., temperature, gas concentration, fluid level) of the bioreactor 308.

The gear system 350 may comprise one or more gears configured to rotate one or more components within the bioreactor module 308. For example, in some variations, one or more gears may be coupled to an impeller of the mixing chamber 342 and/or bioreactor 340. Advantageously, in some variations, the gear system 350 may be optimized to facilitate motion of the impellers of both of the mixing chamber 342 and bioreactor 340. Accordingly, the impellers of the mixing chamber 342 and bioreactor 340 may share components, which may reduce the number of components of the bioreactor module 308 and/or operational complexity thereof. For example, a first gear (e.g., a drive gear) may be coupled to each of a second gear (e.g., a first driven gear) and a third gear (e.g., a second driven gear). The first gear may receive an input, such that the first gear may rotate in response to the input. For example, the input may be provided via one or more electromagnets coupled to the first gear, such that providing a current to the electromagnet(s) may rotate the first gear. In another example, the input may be provided via a motor be coupled to the first gear such that actuating the motor may rotate the first gear. The rotation of the first gear may cause each of the second and third gears to rotate. The amount of rotation may be determined by a gear ratio defined by a number of gear teeth of the drive gear to the number of gear teeth of the driven gear. In some variations, the gear ratio may be between about 5:1 to about 1:1. The gear ratio may be optimized to minimize the amount of electrical power required to actuate the gear system 350. For example, in some variations, the gear ratio may be 5:1, 4:1, 3:1, 2:1 or 1:1. In some variations, there may be between 1 and 10 gears, such as 1, 2, 3, 4, 5, 6, 7, 8, 9, or 10 gears. Each of the gears may be coupled together, such that rotating one gear may cause every other gear to rotate. In further variations, each of the gears may not be coupled together, such that each gear may be independently rotated in response to an input. For example, each gear may be coupled to an electromagnet, such that each electromagnet may be controlled by an electrical signal.

The port system 354 may be configured to transfer one or more gases to and/or from one or more of the bioreactor 340, mixing chamber 342, first thermal compartment 344, second thermal compartment 346, and third thermal compartment 348. The port system 354 may be configured to facilitate a gaseous environment within the bioreactor module 308 suitable for cell growth and/or culturing.

1.1.5. Flow Cell

The flow cell 310 may generally include a fluid channel having at least one port configured to couple to the tube 304 such that a fluid (e.g., cell solution) may flow into and out of the flow cell 310 via the tube 304. In some variations, the flow cell 310 may be a component of a cell sorting module (e.g., cell sorting module 166 of FIG. 1). While flow cell 310 may be described herein with respect to a cell sorting module, it should be understood that the flow cell 310 may be a discrete component of a cell processing cartridge, or may be a component configured to be utilized for a plurality of cartridge modules.

Figure 3E:
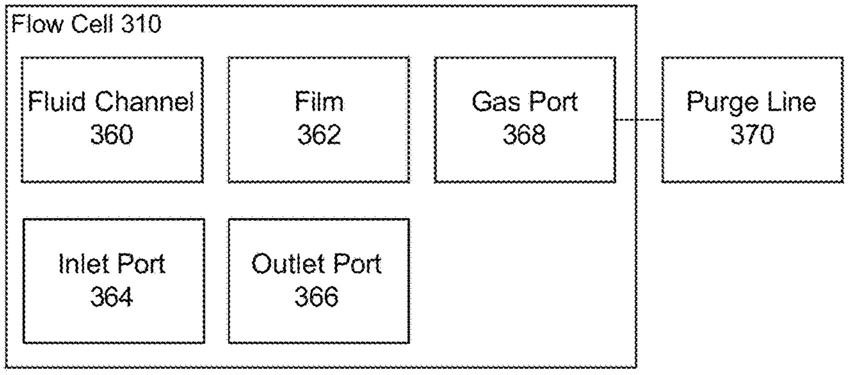
FIG. 3E is a block diagram of an illustrative variation of a flow cell of the transduction system of FIG. 3A.

FIG. 3E is a block diagram of an illustrative variation of the flow cell 310 of the transduction system 300 of FIG. 3A. As shown, the flow cell 310 may include one or more of a fluid channel 360, a film 362, an inlet port 364, an outlet port 366, the gas port 368, and a purge line 370, each of which are described in detail below with respect to FIGS. 4A-4D. In some variations, the flow cell 310 may include a single port configured to direct fluid in and out of the flow cell 310. That is, in some variations, the inlet port 364 and the outlet port 366 may be the same port. Further, in some variations, the transduction system 300 may include a plurality of flow cells 310, such as one or more flow cells, or at least one flow cell.

In some variations, the flow cell 310 may also include sensors configured to aid in pumping fluid into and out of the flow cell 310. For example, the flow cell 310 may include one or more sensors, such as one or more bubble sensors coupled to one or more tubes of the flow cell (e.g., tube 304 of FIG. 3A, fluid conduits 454*a*, 454*b* of FIG. 4D). The bubble sensor may detect a cell solution entering the flow cell 310 and cause the pump module 306 to temporarily stop pumping the solution throughout the transduction system 300 (e.g., via the bioreactor module 308). Then, the cell solution may continue to flow along the fluid pathway for transduction, out of the flow cell 310, and repeat the cycle through the transduction system 300.

Figure 4A:
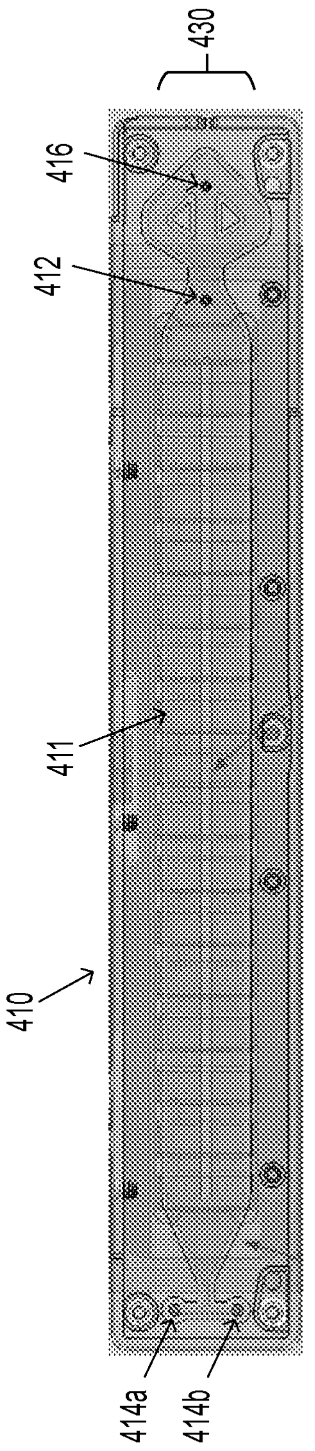
FIG. 4A is a top view rendering of an illustrative variation of a flow cell.

Referring now to FIG. 4A, a rendering of an exemplary variation of a flow cell 410 is shown. The flow cell 410 may comprise a fluid channel 411, an inlet port 412, one or both of a first outlet port 414*a* and a second outlet port 414*b*, and optionally a gas port 416. The inlet port 412 may be positioned at a first end of the fluid channel 411. The gas port 416 may also be positioned at the first end of the fluid channel 411. The gas port 416 may be positioned such that any fluid (e.g., gas) introduced via the gas port 416 may flow past the inlet port 412. The positioning of the gas port relative to the inlet port may increase the efficacy of the fluid introduced via the gas port in removing any cellular material in any location within the fluid channel 411. The outlet ports 414*a*, 414*b* may be positioned at a second end of the fluid channel 411, where the second end is opposite the first end. Accordingly, fluid (e.g., cell suspension) may flow into the inlet port 412, along the entire fluid channel 411, and out of the outlet ports 414*a*, 414*b*. In some variations, the transduction systems described herein (e.g., transduction system 300) may include a first tube (e.g., tube 304 of FIG. 3A) configured to couple to the inlet port 412 and a second tube (e.g., tube 304 of FIG. 3A) configured to couple to one of the first and second outlet ports 414*a*, 414*b*. For example, in variations where the flow cell 410 may be a component of a cell sorting module, the flow cell 410 may include the gas port 416 to transfer a fluid (e.g., gas) into the fluid channel 411 to remove waste of the cell solution from the fluid channel 411.

Figure 4B:
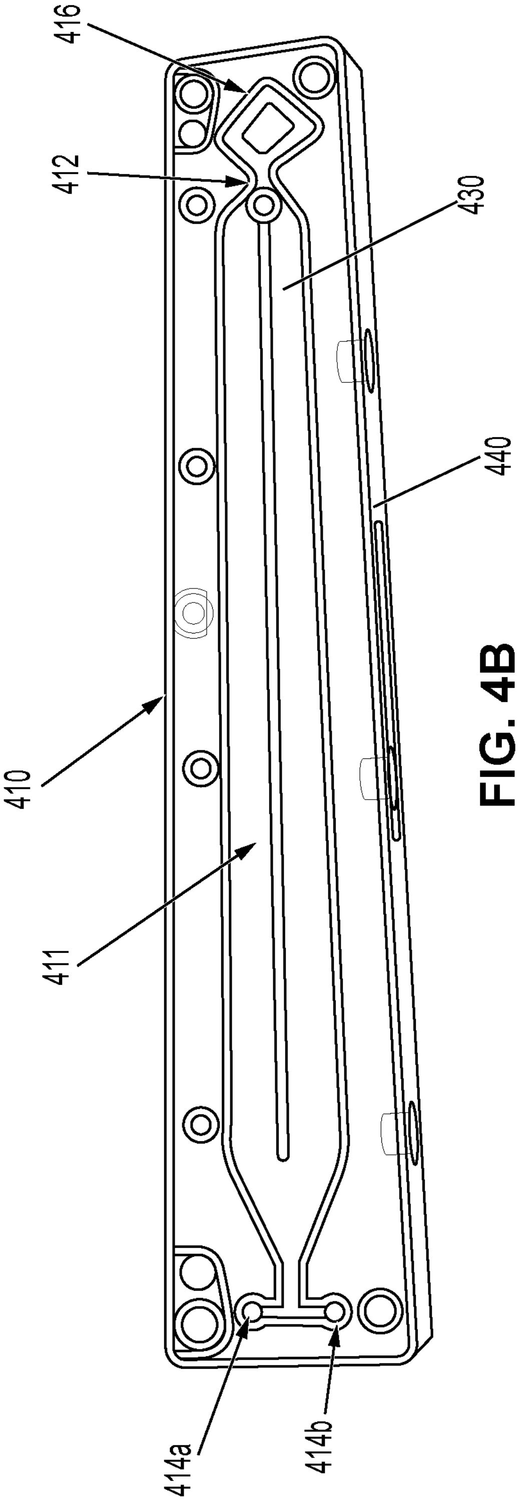
FIG. 4B is a top view of an illustrative variation of a flow cell.

FIG. 4B shows another exemplary variation of the flow cell 410. As shown, the flow cell 410 may comprise a film 440 configured to cover a fluid channel 411. The film 440 may be configured to provide a fluid barrier between the fluid channel 411 and an external environment, such that a cell suspension may flow through the fluid channel 411 without leaking. Therefore, the film 440 may advantageously have a thickness sufficient to withstand pressures, temperatures, and/or flow rates associated with the cell suspension without cracking, fracturing, shattering, or otherwise breaking. For example, the film 440 may comprise a thickness of between about 50 microns to about 500 microns, about 100 microns to about 500 microns, about 200 microns to about 400 microns, or about 250 microns to about 350 microns, including about 100 microns, about 200 microns, about 300 microns, or about 400 microns. The fluid channel 411, which may be covered by the film 440, may define a volume configured to contain the batch of cell suspension. For example, in some variations, the fluid channel 411 may be configured to hold a volume of fluid between about 0.5 mL to about 25 mL, about 1 mL to about 20 mL, or about 1 mL to about 15 mL, including about 1 mL, about 5 mL, about 8 mL, about 10 mL, about 12 mL, or about 15 mL of fluid. In some variations, a cell suspension may comprise a volume that may be the same as the fluid channel volume, or may be less. For example, in some variations, the batch of cell suspension may comprise a volume of about 0.5 mL to about 25 mL, about 1 mL to about 15 mL, about 6 mL to about 12 mL, or about 8 mL to about 10 mL, including about 5 mL, about 8 mL, about 9 mL, about 10 mL, or about 12 mL. Accordingly, the volume of cell suspension may be configured to avoid a buildup of pressure applied to the sidewall(s) of the flow cell, which may otherwise occur if the volume of cell suspension is greater than the volume of the flow cell.

Like the tube 304, the fluid channel 411 may have a width or diameter (e.g., inner width or inner diameter in the case of a fluid channel having a circular cross-section) of between about 1 mm and about 20 mm, such as between about 1.25 mm and about 15 mm, between about 1.5 mm and about 10 mm, between about 1.75 mm and about 5 mm, between about 2 mm and about 4 mm, or between about 2.5 mm and about 3.5 mm. For example, the width or diameter of the fluid channel 411 may be between about 1.5 mm and about 3.5 mm, such as between about 1.57 mm and about 3.18 mm. fluid channel 411 may have circular, oval, square, or rectangular cross-sectional shape. In some variations, a circular fluid channel 411 may have a diameter of between about 1 mm and about 10 mm. In some variations, an oval fluid channel 411 may have a first diameter of between about 1 mm and about 10 mm, and a second diameter of between about 1 mm and about 30 mm. In some variations, a square fluid channel 411 may have a width of between about 1 mm and about 10 mm. In some variations, a rectangular fluid channel 411 may have a first width of between about 1 mm and about 10 mm, and a second width of between about 1 mm and about 30 mm. Each of the diameter of the circular fluid channel, the first diameter of the oval fluid channel, the width of the square fluid channel, and the first width of the rectangular fluid channel may have a diameter or width, respectively, of between about 1.5 mm and about 3.5 mm, such as between about 1.57 mm and about 3.18 mm.

The fluid channel 411 may have a length of between about 10 mm and about 5,000 mm, such as between about 25 mm and about 2,500 mm, between about 50 mm and about 1,000 mm, between about 100 mm and about 750 mm, between about 150 mm and about 500 mm, or between about 200 mm and about 250 mm. Moreover, the fluid channel 411 may have a surface area (e.g., an internal surface area of the length of the fluid channel 411) of between about 1 $mm^2$ and about 50 $mm^2$, such as between about 3 $mm^2$ and about 40 $mm^2$, between about 5 $mm^2$ and about 30 $mm^2$ between about 7 $mm^2$ and about 20 $mm^2$, between about 9 $mm^2$ and about 18 $mm^2$, between about 10 $mm^2$ and about 17 $mm^2$, between about 11 $mm^2$ and about 16 $mm^2$, between about 12 $mm^2$ and about 15 $mm^2$, or between about 13 $mm^2$ and about 14 $mm^2$. Further, the fluid channel 411 may define a volume (e.g., a volume of a lumen along the length of the fluid channel 411) of between about 1 μL and about 250 μL, such as between about 2 μL and about 100 μL, between about 4 μL and about 80 μL, between about 8 μL and about 60 μL, between about 10 μL and about 40 μL, between about 12 μL and about 20 μL, or between about 14 μL and about 18 μL.

Figure 4C:
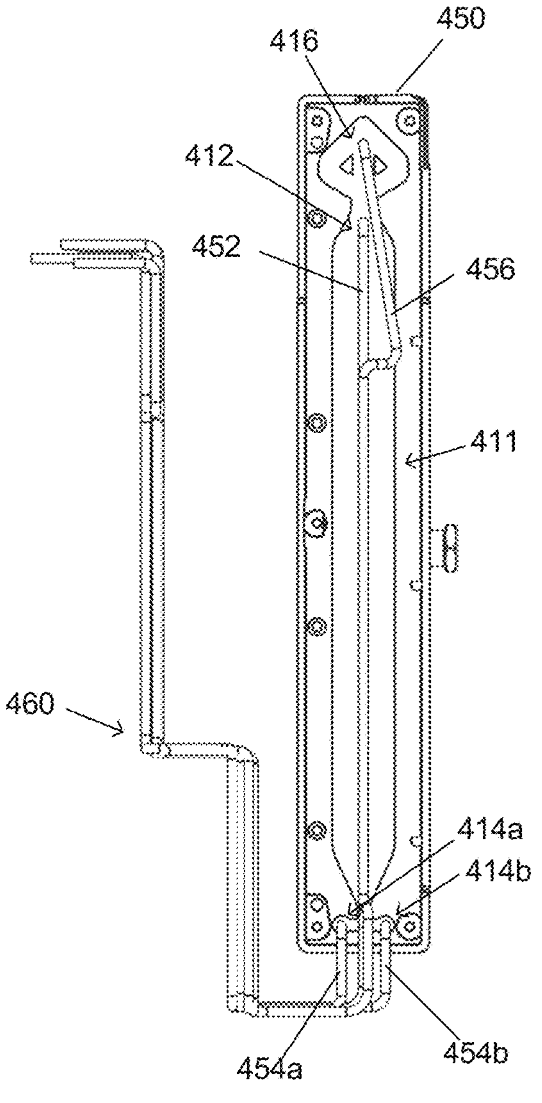
FIG. 4C is a top view rendering of another variation of a flow cell.
Figure 4D:
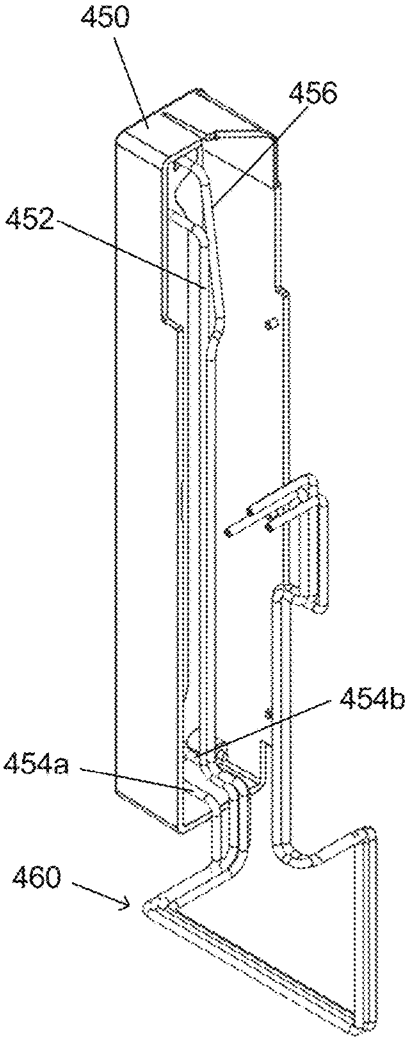
FIG. 4D is a perspective view of the flow cell shown in FIG. 4C.

FIGS. 4C and 4D show the flow cell 410 coupled to a plurality of fluid conduits (e.g., tubes) 460, which may fluidically connect the flow cell 410 to a fluidic manifold (not shown). The flow cell 410 may comprise a flow cell body 450 configured to house the fluid channel 420 and at least a portion of the fluid conduits 460 connected to the flow cell 410, which may prevent damage to a connection point between a fluid conduit and the flow cell 410. As shown, the fluid conduits 460 of the flow cell 410 may comprise an inlet fluid conduit 452 coupled to the inlet port 412, one or both of a first outlet fluid conduit **454*a* coupled to the outlet port 414*a* and a second outlet fluid conduit 454*b* coupled to the outlet port 414*b*, and optionally a purge line 456 coupled to the gas port 416. The inlet fluid conduit 452 may be configured to transfer a fluid, such as an unsorted cell suspension, into the fluid channel 411 via the inlet port 412. The outlet fluid conduits 454*a*, 454*b* may be configured to transfer a fluid, such as a cell suspension undergoing transduction, out of the fluid channel 411 via the outlet ports 414*a*, 414*b*. The purge line 456 may be configured to transfer a fluid (e.g., gas) into the fluid channel 411 via the gas port 416. For example, the purge line 456 may be used to introduce air into the fluid channel 411 after the non-targeted material of the cell suspension may be removed from the fluid channel 411, such that only targeted cells, including stuck cells, remain within the fluid channel 411. Accordingly, the air introduced via the purge line 456 may be configured to loosen the stuck cells, such that substantially all targeted cells may be removed from the fluid channel 411. For example, the purge line 456 may introduce air at a flow rate of between about 1 mL/min and about 40 mL/min and/or a pressure of between about 1 psi and about 10 psi. The volume of air introduced by the purge line 456 may be between about 6 mL and about 120 mL. However, it should be understood that in some variations, the flow cell 410 may not include each of the first outlet fluid conduit 454*a* coupled to the outlet port 414*a* and the second outlet fluid conduit 454*b* coupled to the outlet port 414*b*, and/or may not include the purge line 456 coupled to the gas port 416**.

The fluid conduits 452, **454*a*, 454*b*, 456 may each have dimensions (e.g., diameter, length, etc.) configured to facilitate fluid transfer to and/or from the flow cell 410 in accordance with a pre-determined flow rate in accordance with a predetermined workflow. For example, a diameter of each fluid conduit 452, 454*a*, 454*b*, 456 may be determined to minimize pressure drop of a fluid flowing therethrough. The diameter of each fluid conduit 452, 454*a*, 454*b*, 456 may be the same or different as each other. In some variations, the diameter of each fluid conduit 452, 454*a*, 454*b*, 456 may be between about 1 mm and about 4 mm. For example, in some variations, the diameter of one or more of the fluid conduits 452, 454*a*, 454*b*, 456 may be about 1 mm, about 1.5 mm, about 2 mm, about 2.5 mm, about 3 mm, about 3.5 mm, or about 4 mm. The flow rate in and/or out of the flow cell 410** may be between about 1 mL/min and about 100 mL/min, between about 2 mL/min and about 75 mL/min, between about 3 mL/min and about 50 mL/min, between about 4 mL/min and about 25 mL/min, or between about 5 mL/min and about 10 mL/min, including about 4 mL/min, about 8 mL/min, about 10 mL/min, about 20 mL/min, and about 30 mL/min. For example, the flow rate in and/or out of the flow cell 410 may be about 8.6 mL/min, such as about 8.683 mL/min.

Methods for Automated Cell Transduction

Figure 5:
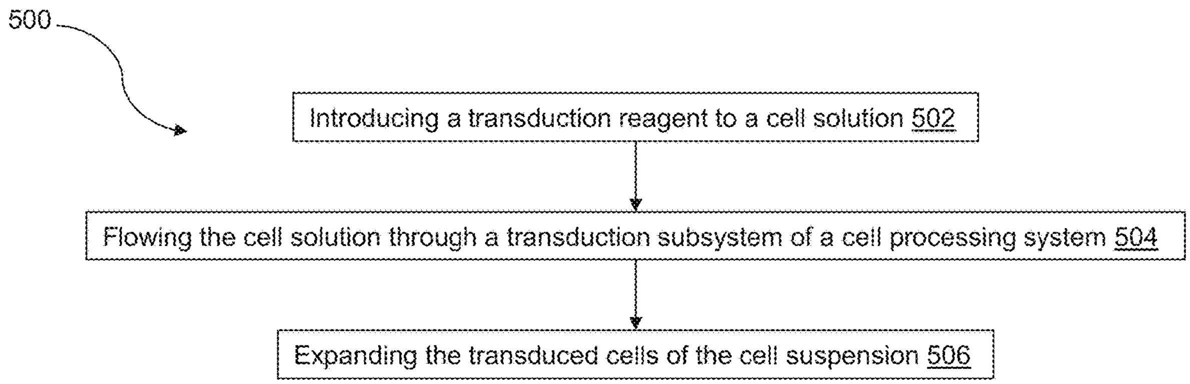
FIG. 5 is a flowchart of an illustrative variation of a method for transducing cells within a cell processing system.

Generally, the systems described herein may perform one or more methods for cell processing, including one or more methods for automated transduction of cells. FIG. 5 provides a flowchart of an illustrative variation of a method for transducing cells within the systems described herein. Although FIG. 5 provides three steps 502, 504, 506 of the method 500, it should be understood that not all of these steps may be required to carry out a cell processing protocol. Similarly, one or more additional steps, like those described below, may be incorporated into the method 500.

As shown, method 500 may include introducing 502 a transduction reagent into a cell solution. In some variations, the transduction reagent may be introduced to a cell solution within a bioreactor module of a cartridge for cell processing, such as a bioreactor or a mixing chamber of the bioreactor module. In some variations, an impeller of the bioreactor module may be employed to prevent the cell solution containing the transduction reagent from setting at the bottom of the bioreactor or mixing chamber. In some variations, the cells of the cell solution may be activated via cell specific activating reagents prior to the introducing 502. For example, a cell solution including T-cells may be activated prior to transduction to increase susceptibility of the T-cells toward transduction. Additionally, or alternatively, the cells of the cell solution may optionally be isolated from blood via apheresis prior to the introducing 502.

Next, the method 500 may include flowing 504 the cell solution through a transduction system of a cell processing system to achieve a desired transduction efficiency. Typically, the flowing 504 may include flowing the cell solution through the transduction system for a predetermined time period (a first time period), such as between about 30 minutes and about 180 minutes, or between about 60 minutes and about 90 minutes. In some variations, the flowing 504 may include transferring the cell solution from the bioreactor or mixing chamber of the bioreactor module to the flow cell via a fluidic manifold of the cell processing cartridge, and transferring the cells from the flow cell to the mixing chamber or bioreactor via the fluidic manifold of the cell processing cartridge. In some variations, the cell solution may be fluidically exchanged between the bioreactor module and the flow cell any number of times during the flowing 504. That is, each of the transferring steps may be repeated any number of times throughout the flowing 504. For example, the number of transfers of the cell solution between the bioreactor module and the flow cell may depend on a length of the first time period and a flow rate of the cell solution throughout the transduction system. In some variations, the flow rate may be constant. For example, one or both of the pump module and the fluidic manifold of the transduction system may be configured to maintain a constant flow rate (e.g., at least 8,600 μL/min, such as about 8,683 μL/min). Moreover, in some variations, the flowing 504 may include flowing a cell solution of a first volume through the transduction system in one or more batches, each having a second, smaller volume of fluid. In some variations, each of a plurality of second, smaller volumes of fluid may have a same or substantially similar volume, such as about 10 mL. In some variations, the predetermined time period for transduction may be the same for each of the one or more batches (e.g., about 60 minutes per batch). In some variations, after the flowing 504 has been performed for a given batch of a plurality of batches of cell solution, the given batch may be pumped to an intermediate container while any remaining batches of the plurality of batches are flowed 504 through the transduction system.

In some variations, one or both of the desired transduction efficiency and the first time period may be set and/or modified by an operator or by the cell processing system (e.g., by a controller of the system) prior to the flowing 504. Additionally, or alternatively, one or more measurements or estimations of transduction efficiency may be made prior to, during, and/or following the flowing 504. For example, techniques for real-time assessment of transduction efficiency may include real-time quantitative PCR approaches and/or real-time imaging techniques (e.g., using fluorescence microscopy and/or flow cytometry) may be employed by one or both of the cell processing system and an operator for real-time evaluation of viral titer of the cells. In some variations, one or more real-time assessments of transduction efficiency may be compared to the desired threshold for transduction efficiency to inform whether a subsequent step of the cell processing workflow may being. Oppositely, in some variations, measurements or estimations of transduction efficiency may not be made prior to, during, and/or following the flowing 504, and the cell processing workflow may continue after the flowing 504 regardless of the transduction efficiency achieved during the flowing 504.

Moreover, in some variations, a priming step may occur prior to the flow 504. For example, fluid (e.g., cell culture media) may be used to prime at least a portion of the fluid pathway of the transduction system, such as to prime the tube fluidically coupling the fluidic manifold to the flow cell. In some variations, during priming, the fluid may flow through the system for between about 10 seconds and about 10 minutes, such as for about 30 seconds, about 45 seconds, about 60 seconds, about 2 minutes, about 5 minutes, or about 10 minutes.

Then, the method 500 may include expanding 506 the transduced cells of the cell solution within the cell processing system. In some variations, the expanding 506 may include conveying the solution to the bioreactor module (e.g., to a mixing chamber, intermediate container, or bioreactor of the bioreactor module) via the fluidic manifold, operating a robot of the cell processing system to move the cartridge to the bioreactor instrument (e.g., bioreactor docking station module configured to engage with the bioreactor module) so that the bioreactor instrument interfaces with the bioreactor module, and further operating the bioreactor instrument to cause the bioreactor module to allow the cells to expand by cellular replication. For example, operating the bioreactor instrument may include providing closed-loop control of one or more of temperature, dissolved oxygen concentration, acidity (pH), and mixing intensity for the bioreactor. In some variations, the expanding 506 may be performed for a predetermined time period (second time period). For example, the second time period may be between about 1 day and about 1 month, such as between about 2 days and about 2 weeks, between about 3 days and about 11 days, between about 4 days and about 10 days, or between about 5 days and about 7 days.

In some variations, the expanding 506 may be a conditional step of the method 500. For example, as described above, in some variations, one or more real-time assessments of transduction efficiency may be compared to a predetermined threshold for transduction efficiency to inform whether a subsequent step of the cell processing workflow, such as the expanding 506, may begin. Accordingly, the expanding 506 may depend on a success (based on transduction efficiency) of the flowing 504. Oppositely, in some variations, the expanding 506 may always occur after the flowing 504, regardless of the transduction efficiency achieved during the flowing 504.

In some variations, following prior to, in between, or following any of the steps 502, 504, 506 of the method 500, waste from a previously transduced cell solution may be purged from the transduction system. For example, a purge line of the flow cell may be used to direct fluid (e.g., gas, such as air) flow toward a waste compartment of a reagent vault of the cell processing system. The purging may have a duration of between about 10 seconds and about 10 minutes, such as for about 10 seconds, about 15 seconds, about 30 seconds, about 45 seconds, about 1 minute, or about 2 minutes. In some variations, cell solution waste may be purged from the transduction system between transduction processes for each of a plurality of batches of a cell solution.

Example 1

A comparison of two experimental setups and methods for enhanced transduction of cells with green fluorescent protein (GFP), a lentiviral vector, within an automated cell processing system and two conventional approaches for the transduction are described below with reference to FIGS. 6A-8B. In particular, the transduction efficiencies achieved after using the two novel methods described below were compared to those determined for each of a static method and a centrifugation method for transduction. The transduction efficiencies were determined for both of days 5 and 7 following the transduction procedure using flow cytometry.

Figure 6:
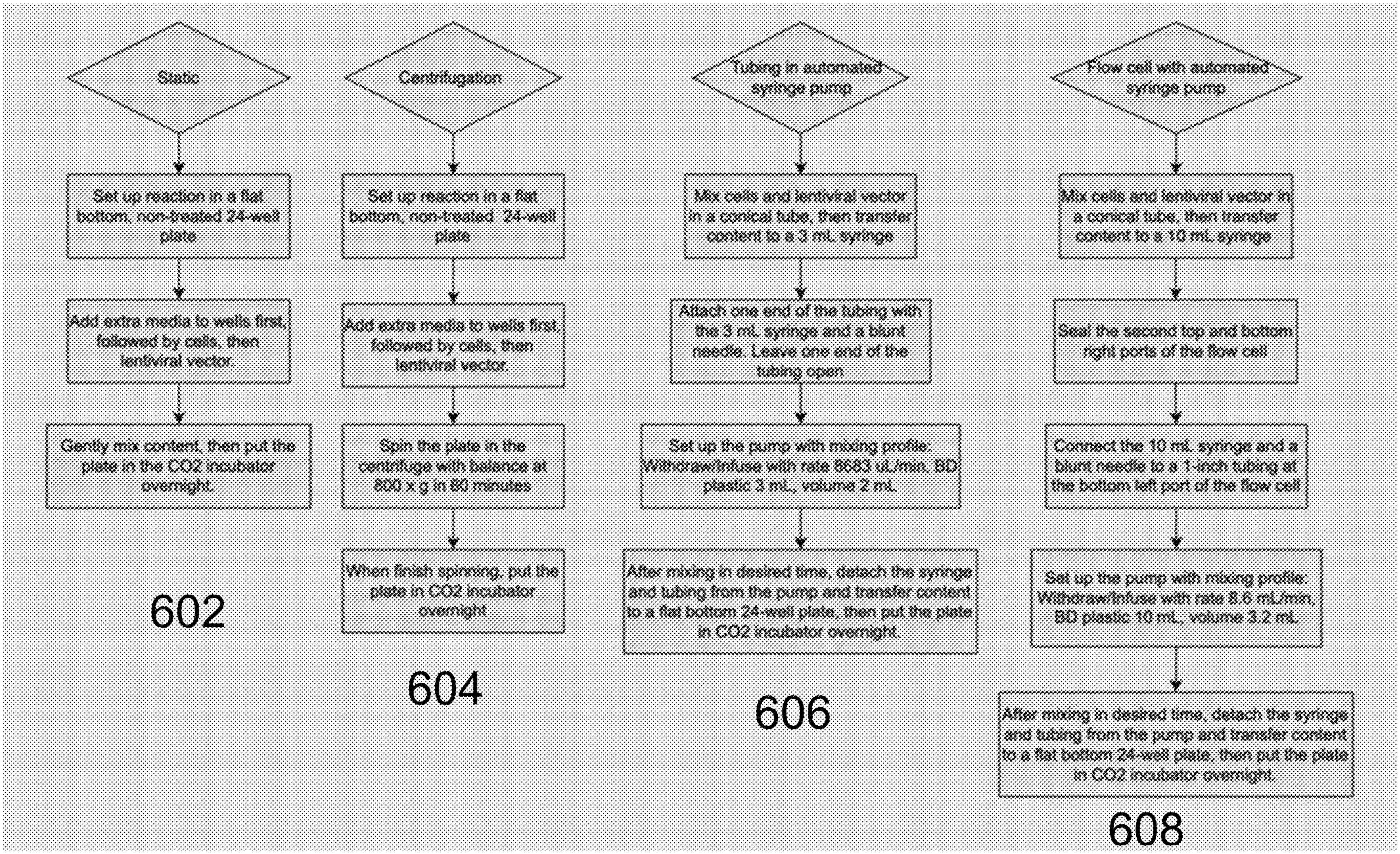
FIG. 6 shows four illustrative variations of an experimental workflow for experiments described in Example 1, comparing GFP transduction protocols of a cell processing system.

FIG. 6 shows four flowcharts of illustrative variations of the experimental workflow the four corresponding experiments described below.

A first experiment 602 tested static transduction (conventional method) of cells with GFP in a flat bottom, non-treated 24-well plate. First, culture media was added to the wells. Second, cells were added to the wells. Third, the lentiviral vector was added to the wells. The contents of the wells were then gently mixed and the plate was placed into a CO2 incubator overnight.

A second experiment 604 tested centrifugation transduction (conventional method) of cells with GFP in a flat bottom, non-treated 24-well plate. First, culture media was added to the wells. Second, cells were added to the wells. Third, the lentiviral vector was added to the wells. Next, the plate was spun in a centrifuge with balance at 800×g for 60 minutes. After centrifugation, the plate was placed into a CO2 incubator overnight.

Figure 7A:
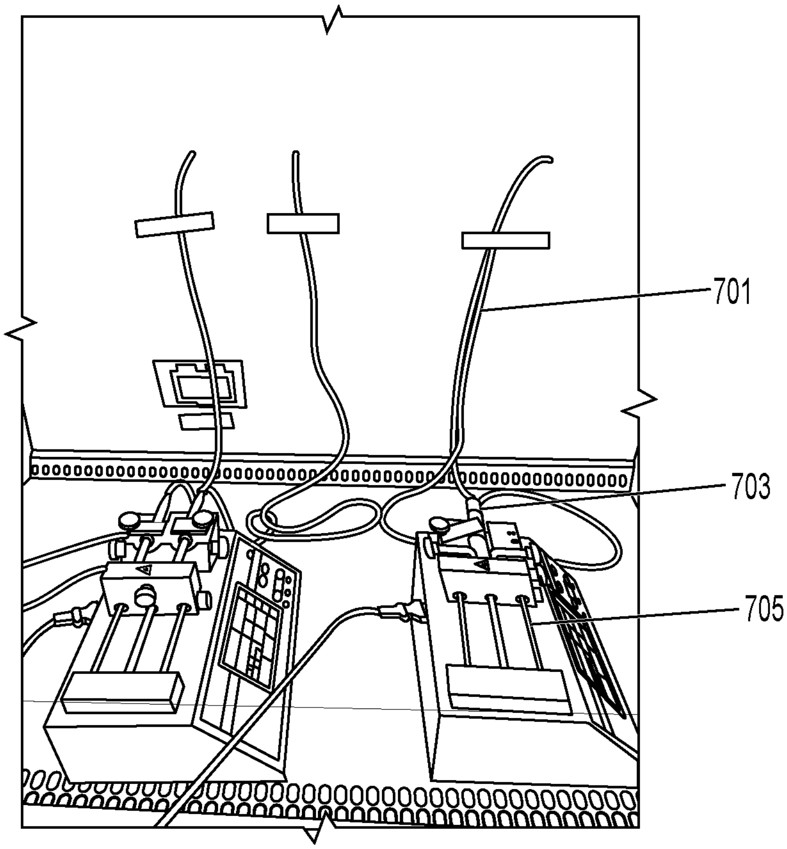
FIGS. 7A-7B show variations of an experimental setup for experiments described in Example 1, comparing GFP transduction protocols of a cell processing system.
Figure 8A:
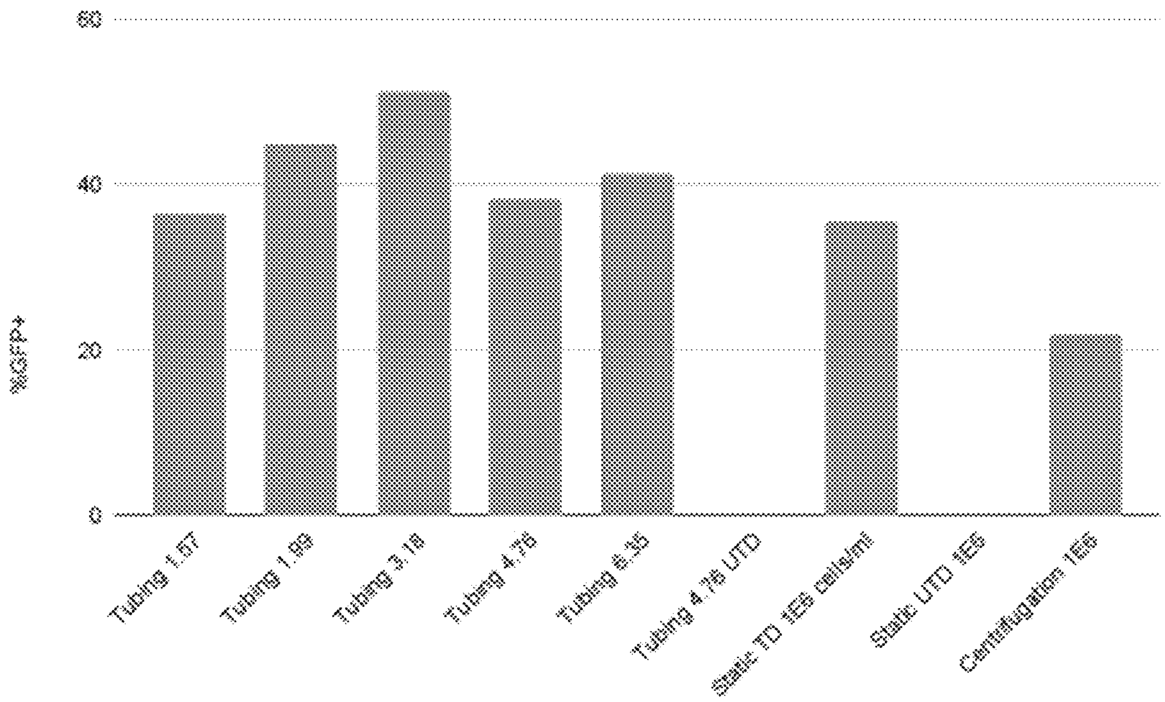
FIGS. 8A-8B show results of experiments described in Example 1, comparing GFP transduction protocols of a cell processing system.

A third experiment 606 tested transduction of cells with GFP using tubing connected to an automated syringe pump. Various tube diameters ranging from 1.57 mm to 6.35 mm were tested with the following procedure. First, a 2 mL solution including the vector and cells were mixed in a conical tube, and then the solution was transferred to a 3 mL plastic syringe. Second, one end of the tubing was attached to the syringe and a blunt needle, while the opposite end of the tubing was left open. Next, the pump was programed to withdraw/infuse from the syringe at a rate of 8,683 μL/min. After mixing for 90 minutes, the syringe was detached from the pump and the solution was transferred to a flat bottom, non-treated 24-well plate which was placed into a CO2 incubator overnight. Referring now to FIG. 7A, an exemplary variation of an experimental setup for the third experiment is shown, including the tubing 701, syringe 703, and pump 705. Below, Table 1 shows the experimental parameters used to calculate the surface area to volume ratio of the tubing 701 for each of five trials of the third experiment 606. Additionally, FIG. 8A depicts a bar graph comparing the transduction efficiency achieved via each of the five trials of the third experiment to the transduction efficiency achieved via the first and second experiments.

TABLE 1

| Inner diameter (mm) | Length (mm) | Surface area ($mm^2$) | Volume in 1 mm (μL) | Volume of cells (μL) | Number of cells | Surface area/volume ($mm^2$/mL) |
|---|---|---|---|---|---|---|
| 1.57 | 1000 | 4.95 | 1.95 | 2,000 | $6 \times 10^6$ | 5080 |
| 1.99 | 610 | 6.22 | 3.08 | 2,000 | $6 \times 10^6$ | 4038 |
| 3.18 | 250 | 9.97 | 7.92 | 2,000 | $6 \times 10^6$ | 2520 |
| 4.76 | 120 | 15.0 | 17.8 | 2,000 | $6 \times 10^6$ | 1680 |
| 6.35 | 62 | 20.0 | 31.7 | 2,000 | $6 \times 10^6$ | 1260 |

Figure 7B:
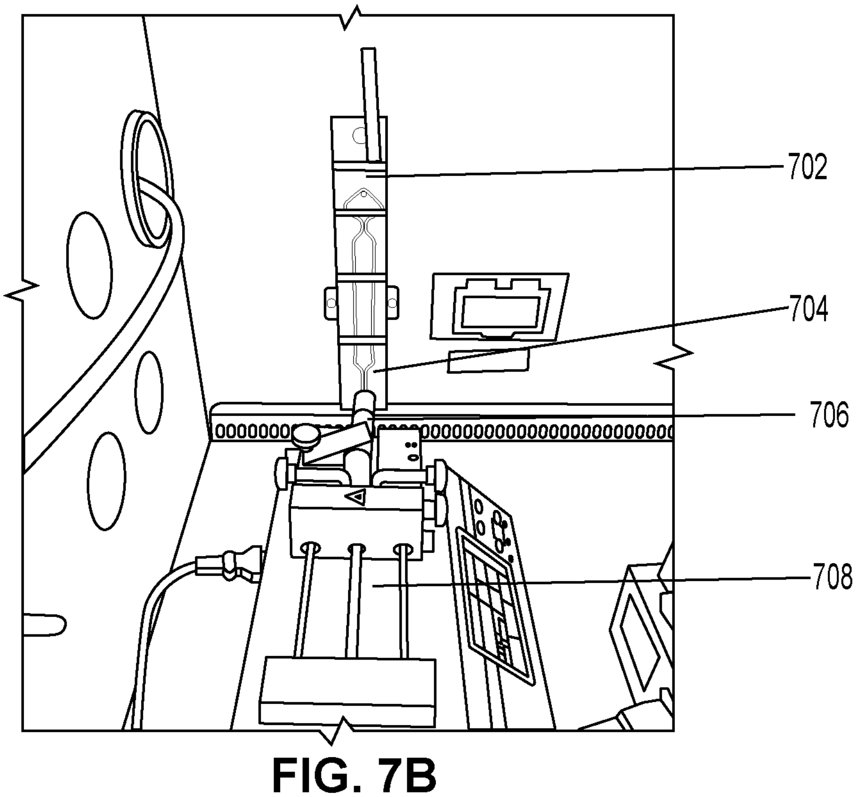

Referring again to FIG. 6, a fourth experiment 608 experiment tested transduction of a lentiviral vector to cells using a flow cell connected to an automated syringe pump at various flow rates (e.g., constant and variable) and for various durations. First, a 3.2 mL solution including the vector and cells were mixed in a conical tube, and then the solution was transferred to a 10 mL plastic syringe. Second, the second top and bottom right ports of the flow cell were sealed. Next, the 10 mL syringe and a blunt needle were connected to a 1 inch tube at the bottom left port of the flow cell. Then, the pump was programed to withdraw/infuse from the syringe at a rate of between 5 mL/min and 100 mL/min. During some trials, the flowrate was kept constant, while during other trials, the flowrate was varied. After mixing for between 30 and 180 minutes, the syringe and tubing were detached from the pump and the solution was transferred to a flat bottom, non-treated 24-well plate which was placed into a CO2 incubator overnight. FIG. 7B shows an exemplary variation of an experimental setup for the fourth experiment, including the flow cell 702, tubing 704, syringe 706, and pump 708. The features of the fourth experiment were designed to replicate features found in the cell processing cartridge described herein throughout. For example, the experimental tubing may represent as a portion of the fluidic manifold (e.g., the tube coupled to the fluidic manifold). The flow cell may represent the flow cell described herein throughout.

Figure 8B:
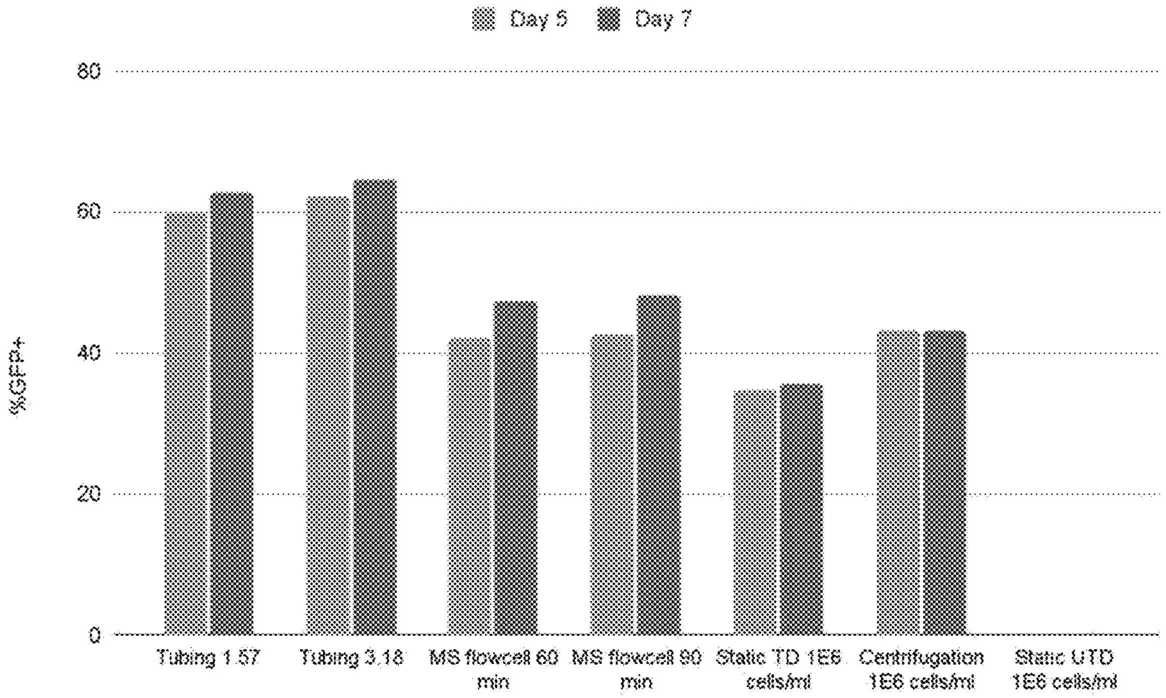

FIG. 8B is a bar graph comparing the results of the most efficient trials of the third and forth experiments to the most efficient trials of the first and second experiments. As shown, the novel (third and fourth) experiments achieved greater transduction efficiencies compared to either of the static (first) experiment or the centrifugation (second) experiment. Additionally, the experiments showed that flowing cells in a confined space (e.g., within a tube—with or without connecting to a flow cell) with a particular surface area to volume ratio for a certain period of time may achieve a transduction efficiency of between 50-60%, and the transduction efficiency may be an improvement of greater than 10% efficiency compared to a static transduction process. Preferential surface area to volume ratios of the confined space are between about 1,260 $mm^2$/mL and about 5,080 $mm^2$/mL.

The surface area to volume ratio may be based on the width or diameter of the confined space. Accordingly, preferential widths or diameters for the confined space are shown to be those between about 1.57 mm and about 3.18.

Finally, Experiment 1 revealed that flowing cells through tubing of 1.57 mm and 3.18 mm diameter for a period of 90 minutes resulted in a higher transduction efficiency than any of the other scenarios. For example, flowing cells through tubing of 3.18 mm diameter for a period of 90 minutes resulted in the greatest transduction efficiency of up to 64.6%.

All references cited are herein incorporated by reference in their entirety.

Throughout this application, the term "about" is used to indicate that a value includes the inherent variation of error for the device, or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

Although the foregoing variations have, for the purposes of clarity and understanding, been described in some detail by illustration and example, it will be apparent that certain changes and modifications may be practiced and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described herein, the steps of the methods may not be performed sequentially. Some steps are optional such that every step of the methods may not be performed.

What is claimed is:

1. A method for cell processing comprising:

introducing a viral vector into a cell solution within a bioreactor module of a cell processing cartridge;

flowing the cell solution through a flow cell of the cell processing cartridge, wherein the cell solution is flowed through at least one tube having a surface area to volume ratio of between about 1,260 $mm^2$/mL and about 5,080 $mm^2$/mL for a first time period to achieve a viral transduction efficiency of at least 50%, wherein the at least one tube provides a bidirectional flow path for the cell solution between the flow cell and a bioreactor module of the cell processing cartridge, and wherein the first time period is about 60 minutes to about 90 minutes;

maintaining a constant flow rate range of about 5 mL/min to about 10 mL/min of the cell solution through the at least one tube over the entire first time period; and expanding cells of the cell solution within the bioreactor module of the cell processing cartridge for a second time period.

2. The method of claim 1, wherein following the cells through the at least one tube comprises:

transferring the cells from a mixing chamber of the bioreactor module to the flow cell via a fluidic manifold of the cell processing cartridge; and transferring the cells from the flow cell to the mixing chamber via the fluidic manifold of the cell processing cartridge.

3. The method of claim 1, wherein the transduction efficiency is measured.

4. The method of claim 1, wherein the transduction efficiency is estimated.

5. The method of claim 1, wherein the cells flow through the at least one tube via a fluidic manifold of the cell processing cartridge.

6. The method of claim 1, wherein the transduction efficiency is equal to or greater than 60%.

7. The method of claim 1, wherein the transduction efficiency is equal to or greater than 70%.

8. The method of claim 1, wherein the second time period is between about 5 days and about 7 days.

9. The method of claim 1, wherein the cell solution comprises a density of between about $5\times10^5$ cells/mL and about $2\times10^6$ cells/mL.

10. The method of claim 1, wherein the cells comprise T-cells.

11. The method of claim 1 further comprising, prior to flowing the cells through the at least one tube, isolating the cells from blood via apheresis.

12. The method of claim 1, wherein the at least one tube comprises a diameter of between about 1.57 mm and about 3.18 mm.

* * * * *